US008591880B2

(12) United States Patent
Chou et al.

(10) Patent No.: US 8,591,880 B2
(45) Date of Patent: *Nov. 26, 2013

(54) GUT FLORA AND WEIGHT MANAGEMENT

(75) Inventors: Chieh Jason Chou, Chexbres (CH);
David Philippe, Lausanne (CH);
Christian Darlmont, Lausanne (CH);
Fabrizio Arigoni, Tokyo (JP);
Catherine Mace, Lausanne (CH)

(73) Assignee: Nestec S.A., Vevey (CH)

( * ) Notice: Subject to any disclaimer, the term of this patent is extended or adjusted under 35 U.S.C. 154(b) by 154 days.

This patent is subject to a terminal disclaimer.

(21) Appl. No.: 12/673,891

(22) PCT Filed: Jul. 25, 2008

(86) PCT No.: PCT/EP2008/059809
§ 371 (c)(1),
(2), (4) Date: Feb. 17, 2010

(87) PCT Pub. No.: WO2009/024429
PCT Pub. Date: Feb. 26, 2009

(65) Prior Publication Data
US 2011/0123501 A1 May 26, 2011

(30) Foreign Application Priority Data
Aug. 17, 2007 (EP) .................... 07114530

(51) Int. Cl.
*A01N 63/00* (2006.01)
*A01N 63/02* (2006.01)
*A61K 35/00* (2006.01)
*A23C 9/12* (2006.01)
*C12N 1/20* (2006.01)

(52) U.S. Cl.
USPC ......... 424/93.3; 424/93.45; 424/780; 426/61; 435/252.9

(58) Field of Classification Search
None
See application file for complete search history.

(56) References Cited

U.S. PATENT DOCUMENTS

| | | | |
|---|---|---|---|
| 5,593,971 A | 1/1997 | Tschollar et al. | |
| 6,080,401 A * | 6/2000 | Reddy et al. | 424/93.3 |
| 6,525,182 B1 | 2/2003 | Goodman et al. | |
| 6,534,085 B1 | 3/2003 | Zeligs | |
| 6,641,808 B1 * | 11/2003 | Bojrab | 424/93.3 |
| 8,440,178 B2 * | 5/2013 | Darimont et al. | 424/93.3 |
| 2002/0090356 A1 | 7/2002 | Waddell et al. | |
| 2003/0229140 A1 | 12/2003 | Bandyopadhyay et al. | |
| 2004/0235789 A1 | 11/2004 | Day et al. | |
| 2005/0239706 A1 | 10/2005 | Backhed et al. | |
| 2006/0067921 A1 * | 3/2006 | Conway | 424/93.45 |
| 2006/0094672 A1 | 5/2006 | Pasqualini et al. | |
| 2006/0100172 A1 | 5/2006 | Monsan et al. | |
| 2006/0233828 A1 | 10/2006 | Romero | |
| 2010/0061967 A1 | 3/2010 | Rautonen | |
| 2010/0172874 A1 | 7/2010 | Turnbaugh et al. | |

FOREIGN PATENT DOCUMENTS

| | | |
|---|---|---|
| EP | 0573682 | 12/1993 |
| JP | 2006273741 | 10/2006 |
| WO | 2006129092 | 12/2006 |
| WO | 2007043933 | 4/2007 |
| WO | WO 2007043933 A1 * | 4/2007 |

OTHER PUBLICATIONS

Coconnier et al., Antimicrobial Agents and Chemotherapy, 1997, vol. 41, No. 5, pp. 1046-1052.*
Written Opinion for International Application No. PCT/EP 2008/059809 dated Sep. 18, 2008.
Partial European Search Report for Application No. EP 07114530.4/Patent No. 2123 dated Sep. 18, 2008.
Fuller, et al., "Modification of the Intestinal Microflora Using Probiotics and Prebiotics," Scand J. Gastroenterol, vol. 32, Suppl. 222: 28-31, 1997.
Carman, et al., "Antibiotics in the human food chain: Establishing no effect levels of tetracycline, neomycin, and erythromycin using a chemostat model of the human colonic microflora," Regulatory Toxicology and Pharmacology, vol. 43, pp. 168-180, 2005.
Backhed, et al., "The gut microbiota as an environmental factor that regulates fat storage," PNAS, vol. 101, No. 44, pp. 15718-15723, 2004; XP009082227.
Faloon, M.D., "Metabolic Effects of Nonabsorbable Antibacterial Agents," The American Journal of Clinical Nutrition, vol. 23, No. 8, pp. 645-651, May 1970.
"Enterobacteria phage T2" http://en.wikipedia,org/wiki/Enterobacteria_phage_T2", Aug. 21, 2008; XP002492887.
Lang et al., "Gut Microbes May Affect Obesity," vol. 132, No. 3, Mar. 23, 2007, Gastroenterology and Hepatology News, p. 836.
Ley, et al., "Microbial Ecology: Human gut mirobes associated with obesity", NAT JRE, vol. 444, No. 21/28; pp. 1022-1023 Dec. 2006; XP 002492885.
Turnbaugh, et al., "An obesity-associated gut microbiome with increased capacity for energy harvest," Nature Publishing Group, vol. 444, No. 21/28, p. 1027-1031, Dec. 28, 2006; XP-002492885.
Neil Campbell et al., "Enterobacteria phage T2" Aug. 21, 2008— http:// en.wikipedia.org/wiki?Enterobacteria,phase T2—XP-002492887.

(Continued)

*Primary Examiner* — Chris R Tate
*Assistant Examiner* — Douglas F White
(74) *Attorney, Agent, or Firm* — K&L Gates LLP

(57) ABSTRACT

The present invention relates to supporting weight management, weight loss and/or to the prevention and/or treatment of metabolic disorders. In particular the present invention relates to preventing and/or treating metabolic disorders by modulating, in particular reducing the amount of proteobacteria and/or deferribacteres in the gut. One embodiment of the present invention relates to the use of a primary composition comprising an agent that reduces the amount of proteobacteria, preferably gamma-proteobacteria, even more preferred enterobacteria; and/or deferribacteres in the gut for the preparation of a composition to treat or prevent metabolic disorders, to support weight loss and/or to support weight management.

17 Claims, 23 Drawing Sheets

(56) References Cited

OTHER PUBLICATIONS

Gastroeoterology and Hepatology News—Gut Microbes May Affect Obesity p. 836—XP-005930913, Mar. 23, 2007.
Backhed et al., "The gut microbiota as an environmental factor that regulates fat storage", PNAS, 15718-15723 Nov. 2, 2004, vol. 101, No. 44—XP-009082227.
Human gut microbes associated with obesity, 2006 Nature Publishing Group p. 1022-1023—XP-002492886.
Turnbaugh et al., "An obesity-associated gut microbiome with increased capacity for energy harvest", 2006 Nature Publishing Group vol. 644, Dec. 21/28, 2006 , pp. 1027-1031—XP-002492885.
Coconnier et al., "Antibacterial effect of the adhering human *Lactobacillus acidophilus* strain LB", Antimicrobial Agents and Chemotherapy, May 1997, vol. 41, No. 5, pp. 1046-1052.
William Faloon, :"Metabolic Effects of Nonabsorbable Antibacterial Agents", The American Journal of Clinical Nutrition, vol. 23, No. 5, May 1978, pp. 645-651.
Fuller et al., "Modification of the Intestinal Microflora Using Probiotics and Prebiotics", Scand J Gastroenterol 1997:32 Suppl. 222:28-31.
Carman et al., "Antibiotics in the human food chain: Establishing no effect levels of tetracycline, neomycin, and erythromycin using a chemostat model of the human colonic microflora", Science Direct, Regulatory Toxicology and Pharmacology 43 (2005) 168-180.

* cited by examiner

GUT FLORA AND WEIGHT MANAGEMENT

The present invention relates to supporting weight management, weight loss and/or to the prevention and/or treatment of metabolic disorders. In particular the present invention relates to preventing and/or treating metabolic disorders by modulating, in particular reducing the amount of proteobacteria and/or deferribacteres in the gut.

The prevalence of obesity has grown in an alarming rate in the past 20 years. Based on the latest estimate in 2004, in the US alone, 66.3% of adults are either overweight or obese, and 32.2% of adults are classified as obese (Cynthia L. Ogden et al., JAMA 2006 Apr. 5; 295:1549-1555). Both genetic and environmental factors have been shown to cause positive energy balance and obesity. Obesity by itself is only a part of problems. Many other chronic diseases such as type 2 diabetes, certain cancers and cardiovascular diseases are common co-morbidities of obesity. Collectively, all the obesity associated medical issues put a tremendous amounts of pressure on health care systems in many countries. Due to the prevalence of obesity, type 2 diabetes has also become a worldwide health problem. According to an epidemiological study, the projective global prevalence for type 2 diabetic population will reach to 366 million people in 2030 (Sarah Wild et al., Diabetes Care 2004 May; 27:1047-1053). Drug treatments for obesity are available but not very effective and with undesirable side-effects. For the treatment of type 2 diabetes, currently available drugs are capable of managing hyperglycemia of the patients. Still more drugs are under development to improve the safety, efficacy of the medications and convenience to use them by patients. To date, all anti-obesity and anti-diabetic drugs are designed to alter the internal metabolism of patients. Most of these drugs are required to be absorbed and delivered to target organs through blood stream for their efficacy. Safety concerns of such a treatment strategy cannot be ignored. In contrast a novel treatment strategy of obesity and type 2 diabetes focusing on targets outside of human tissues is greatly desirable because the active agents are not required to enter our body, and the safety of the treatments can be improved significantly.

Human beings are superorganisms with a body composed of millions of human cells while many more bacteria live, e.g., in the colon. It has been estimated that more than $10^{13}$ to $10^{14}$ bacteria are alive in a healthy human intestine. Intestinal bacteria can be separated into 2 major divisions, firmicutes and bacteriodetes (Steven R. Gill,et al., Science 2006 Jun. 2; 312: 1355-1359; Peter J. Turnbaugh, et al., Nature 2006 Dec. 21; 444:1027-131). Together, they represent at least 90% of total bacterial population in the gut. The presence of the gut bacteria is a part of normal human physiology and is important for the development of gut functions (Hooper L V et al., Science. 2001 Feb. 2; 291(5505):881-4; Stappenbeck T S, et al., Proc Natl Acad Sci USA. 2002 Nov. 26; 99(24):15451-5), maturation of the immune system (Mazmanian S K, et al., Cell. 2005 Jul. 15; 122(1):107-18), harvesting energy from dietary carbohydrates (Peter J. Turnbaugh, et al., Nature 2006 Dec. 21; 444:1027-131), harvesting essential vitamins (Backhed F, et al., Science. 2005 Mar. 25; 307(5717):1915-20) and metabolizing environmental chemicals in the gut (Nicholson J K, et al., Nat Rev Microbiol. 2005 May; 3(5):431-8). Recent studies further suggested that gut bacteria may be involved in fat storage (Backhed F, et al., Proc Natl Acad Sci USA. 2004 Nov. 2; 101(44):15718-23).

However, until now it has never been taught or suggested to manipulate the composition of gut bacteria to treat or prevent metabolic disorders. To the best knowledge of the inventors it is so far undescribed in the art that the population of gut bacteria, in particular enterobacteria can be manipulated in order to improve the human health, especially in cases of obesity and/or type 2 diabetes.

It was one object of the present invention to improve the management of metabolic disorders by a method that does not require that the active agent is absorbed by the body. Instead the present invention aims to modulate the population of bacteria in the intestine of patients.

Consequently, the object of the present invention is achieved by a use in accordance with claim 1.

One embodiment of the present invention relates consequently to the use of a primary composition comprising an agent that reduces the amount of proteobacteria, preferably gamma-proteobacteria, even more preferred enterobacteria in the gut for the preparation of a composition to treat or prevent metabolic disorders, to support weight loss and/or to support weight management.

Importantly, the present inventors found that this effect of treating or preventing metabolic disorders, to support weight loss and/or to support weight management persisted even after the administration of the composition comprising an agent that reduces the amount of proteobacteria, preferably gamma-proteobacteria, even more preferred enterobacteria in the gut was stopped.

Hence, in one embodiment the use of the present invention is to produce an effect on weight loss, weight management and/or treatment and/or prevention of metabolic disorders that persists after the administration of the composition is discontinued.

This effect may persist at least 3 days, preferably at least a week, more preferably at least 2 weeks, even more preferred at least 4 weeks, most preferred at least 5 weeks after the administration of the composition is discontinued.

One important aspect of the present invention is to understand the influences of different gut bacteria to human health. The inventors were surprised to find that benefits in supporting weight loss and/or weight management and in the treatment and/or prevention of metabolic disorders, in particular weight control and treatment of type 2 diabetes, can be achieved when gut proteobacteria, preferably gamma-proteobacteria, even more preferred enterobacteria are specifically reduced. The amount of proteobacteria, preferably gamma-proteobacteria, even more preferred enterobacteria; and/or deferribacteres may be reduced overall and/or in relation to other kinds of bacteria present in the gut.

One aspect of the present invention is hence a method for supporting weight loss and/or weight management and/or for treating and/or preventing metabolic disorders, the method comprising reducing the amount of proteobacteria and/or deferribacteres; in particular the relative amount of proteobacteria, in the gut.

Consequently, another aspect of the present invention is to reduce specifically the amount of proteobacteria, preferably gamma-proteobacteria, even more preferred enterobacteria; and/or deferribacteres, in relation to the other bacteria in the gut to support weight loss and/or weight management and/or to treat and/or prevent metabolic disorders, in particular to reduce weight gain and improve glucose control in type 2 diabetes.

The inventors have further investigated in detail, how the use of the primary composition of the present invention influences the gut flora, and how the resulting gut flora influences the body weight of mice.

It was found that a primary composition comprising an agent that modifies the ratio of proteobacteria to bacteriodetes and/or the ratio of proteobacteria to firmicutes; and or the ratio of bacteriodetes to firmicutes can be used for example to support weight loss and/or weight management and/or to treat and/or prevent metabolic disorders. For example, the ratio of gamma-proteobacteria to bacteriodetes and/or the ratio of gamma-proteobacteria to firmicutes may be modified.

Optimal results, for example in terms of prevention and treatment of metabolic disorders, were achieved for example, when the ratio of proteobacteria to bacteriodetes was reduced. At the same time the ratio of proteobacteria to firmicutes and/or the ratio of bacteriodetes to firmicutes may be increased.

The present invention consequently also relates to the use of a primary composition comprising an agent that reduces the ratio of proteobacteria to bacteriodetes and/or that increases the ratio of proteobacteria to firmicutes and/or the ratio of bacteriodetes to firmicutes in the gut for the preparation of a composition to treat or prevent metabolic disorders, to support weight loss and/or to support weight management.

For example, the present invention relates to the use of a primary composition comprising an agent that reduces the ratio of gamma-proteobacteria to bacteriodetes in the gut and/or that increases the ratio of gamma-proteobacteria to firmicutes in the gut for the preparation of a composition to treat or prevent metabolic disorders, to support weight loss and/or to support weight management.

A further embodiment of the present invention is the use of an agent selected from the group consisting of bacterial phages, prebiotics, food grade bacteria, in particular probiotics, yeasts, phytochemicals, antibiotics and mixtures thereof for the preparation of a composition to reduce the amount of proteobacteria, preferably gamma-proteobacteria, even more preferred enterobacteria; and/or deferribacteres in the gut. For example the amount of proteobacteria, and/or deferribacteres, in particular the relative amount of proteobacteria, in the gut may be reduced. Further, the ratio of proteobacteria to bacteriodetes may be reduced and/or the ratio of proteobacteria to firmicutes and/or the ratio of bacteriodetes to firmicutes may be increased. For example the ratio of gamma-proteobacteria to bacteriodetes in the gut may be reduced and/or the ratio of gamma-proteobacteria to firmicutes in the gut may be increased.

The composition of bacteria community is measured by annotating bacterial 16S rDNA sequences to the Silva database followed by RDP-II Classifier. The bacterial ratios are calculated by dividing the relative abundance of a specific division of bacterial sequences to the relative abundance of the other specific division of bacterial sequences, for example, the abundance of proteobacteria in % by the abundance of bacteriodetes in %.

For example, the ratio of proteobacteria to bacteriodetes may be reduced to the range of 0-0.5; preferably 0-0.15, even more preferred 0-0.03.

The ratio of proteobacteria to firmicutes may be increased to the range of 0.02-2; preferably 0.1-2, even more preferred 0.5-2.

The ratio of bacteriodetes to firmicutes may be increased to a range of may be increased to the range of 0.5-100; preferably 1-50, even more preferred 1.5-30.

The ratio of gamma-proteobacteria to bacteriodetes may be reduced to the range of 0-0.5; preferably 0-0.1, even more preferred 0-0.03. The ratio of gamma-proteobacteria to firmicutes may be increased to the range of 0.02-2; preferably 0.1-2, even more preferred 0.5-2.

In accordance with this, the relative amount of proteobacteria, and/or deferribacteres to the total amount of bacteria in the gut may be reduced by 1-100%; preferably 50-100%, even more preferred 75-100%. The relative amount of gamma-proteobacteria to the total amount of bacteria in the gut may be reduced by 1-100%; preferably 50-100%, even more preferred 75-100%. The percentages are calculated based on the cfu of the bacterial species present in the gut.

For example, the total amount of gut enterobacteria may be reduced by 1-100%; preferably 50-100%, even more preferred 75-100%.

In the framework of the present invention "reducing the amount of enterobacteria in the gut" means "reducing the amount of alive enterobacteria in the gut". "Reducing the amount of enterobacteria in the gut" may also include reducing the total amount of enterobacteria, dead or alive, in the gut. "Reducing the amount of enterobacteria in the gut" may also relate to "reducing the amount of dead enterobacteria in the gut.

The phylum "Proteobacteria" comprises the classes alpha-, beta-, gamma-, delta- and epsilon-proteobacteria.

Deferribacteres represent a further phylum and are—for example—described in Bergey's Manual of Systematic Bacteriology, 2nd ed., vol. 1 (D. R. Boone and R. W. Castenholz, eds.), Springer-Verlag, New York (2001). pp. 465-466, herewith incorporated herein by reference.

Alpha-Proteobacteria comprise for example Caulobacterales, e.g. *Caulobacter*; Kordiimonadales; Parvularculales; Rhizobiales, e.g. Rhizobia; Rhodobacterales; Rhodospirillales, e.g., *Acetobacter*; Rickettsiales, *Rickettsia*; and Sphingomonadales, e.g., *Sphingomonas*.

Beta Proteobacteria comprise for example Burkholderiales, *Bordetella*; Hydrogenophilales; Methylophilales; Neisseriales, e.g., *Neisseria*; Nitrosomonadales; Rhodocyclales; and Procabacteriales.

Gamma Proteobacteria comprise for example Acidithiobacillales; Aeromonadales, e.g., *Aeromonas*; Alteromonadales, e.g., *Pseudoalteromonas*; Cardiobacteriales; Chromatiales, e.g., purple sulfur bacteria; Enterobacteria, e.g. *Escherichia*; Legionellales, e.g., *Legionella*; Methylococcales; Oceanospirillales; Pasteurellales, e.g., *Haemophilus*; Pseudomonadales, e.g., *Pseudomonas*; Thiotrichales, e.g., *Thiomargarita*; Vibrionales, e.g., *Vibrio*; and Xanthomonadales, e.g., *Xanthomonas*.

Delta Proteobacteria comprise for example Bdellovibrionales, e.g., *Bdellovibrio*; Desulfobacterales; Desulfovibrionales; Desulfurellales; Desulfarcales; Desulfuromonadales, e.g., *Geobacter*; Myxococcales, e.g., Myxobacteria; and Syntrophobacterales.

Epsilon Proteobacteria comprise for example Campylobacterales, e.g. *Helicobacter*.

Further preferably, enterobacteria may be selected from the group consisting of *Alishewanella, Alterococcus, Aquamonas, Aranicola, Arsenophonus, Azotivirga, Blochmannia, Brenneria, Buchnera, Budvicia, Buttiauxella, Cedecea, Citrobacter, Dickeya, Edwardsiella, Enterobacter, Erwinia, Escherichia, Ewingella, Grimontella, Hafnia, Klebsiella, Kluyvera, Leclercia, Leminorella, Moellerella, Morganella, Obesumbacterium, Pantoea, Pectobacterium, Candidatus Phlomobacter, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhabdus, Yersinia, Yokenella* or mixtures thereof.

Particular examples of metabolic disorders that can be treated or prevented by the above use include obesity, insulin resistance, type-2 diabetes, hyperglycemia, hepatic steatosis and combinations thereof.

The use of the present invention is further applicable to treat or prevent weight gain.

The present invention consequently also relates to a use of a primary composition comprising an agent that reduces the amount of proteobacteria, preferably gamma-proteobacteria, even more preferred enterobacteria; and/or deferribacteres in the gut for the preparation of a composition to promote weight loss.

The present invention further relates to a use of a primary composition comprising an agent that reduces the amount of proteobacteria, preferably gamma-proteobacteria, even more preferred enterobacteria; and/or deferribacteres in the gut for the preparation of a composition to support weight management.

"Overweight" is defined for an adult human as having a BMI between 25 and 30.

"Body mass index" or "BMI" means the ratio of weight in kg divided by the height in meters, squared.

"Obesity" is a condition in which the natural energy reserve, stored in the fatty tissue of animals, in particular humans and other mammals, is increased to a point where it is associated with certain health conditions or increased mortality. "Obese" is defined for an adult human as having a BMI greater than 30.

"Weight loss" in the context of the present invention is a reduction of the total body weight. Weight loss may for example refer to the loss of total body mass in an effort to improve fitness, health, and/or appearance.

"Weight management" or "weight maintenance" relates to maintaining a total body weight. For example, weight management may relate to maintaining a BMI in the area of 18.5-25 which is considered to be normal.

"Probiotic" means microbial cell preparations or components of microbial cells with a beneficial effect on the health or well-being of the host. (Salminen S, Ouwehand A. Benno Y. et al "Probiotics: how should they be defined" Trends Food Sci. Technol. 1999: 10 107-10).

"Prebiotic" means food substances intended to promote the growth of probiotic bacteria in the intestines. One example of prebiotics is dietary fibers. Dietary fibers are fibers that are non-digestible by the human body.

"Food grade bacteria" means bacteria that are used and generally regarded as safe for use in food.

The composition of the present invention may be any composition, for example it may be a medicament. As a medicament usually requires supervision by medical personnel, a medicament has the advantage that the success of the use of the present invention can be carefully monitored and—if necessary—the composition can be custom fitted to the needs of the patient to be treated.

In a preferred embodiment of the present invention the composition is a food product. Food products have the advantage that the benefits of the present invention would be available to everybody immediately without requiring a medical prescription. The treatment or prevention of metabolic disorders could be initiated at a much earlier stage. Further in a food product the composition prepared by the use of the present invention would be even more pleasant to consume.

As nowadays metabolic disorders are no longer only a problem of the human population, the food product or the medicament prepared by the use of the present invention may be intended for humans or animals, in particular pets or livestock. Animals may be selected from the group consisting of dogs, cats, pigs, cattle, horses, goats, sheep or poultry. Furthermore, nowadays metabolic disorders are no longer a problem that only concerns the adult population.

Hence, the compositions prepared by the use of the present invention may be intended for infants, children, adolescents and/or adults.

The compositions of the present invention exhibit their beneficial effects at any age of the subject to be treated. Since, however, metabolic disorders are still found mainly in the adult population, it is preferred that the composition prepared by the use of the present invention is intended for adult patients, in particular human adults.

Central to the present invention is the idea of reducing the amount of proteobacteria, preferably gamma-proteobacteria, even more preferred enterobacteria; and/or deferribacteres in the gut. Consequently, any agent or method that is capable of reducing proteobacteria, preferably gamma-proteobacteria, even more preferred enterobacteria; and/or deferribacteres in the gut can be used for the purpose of the present invention. It is preferred, however that the agent capable of reducing the amount of proteobacteria, preferably gamma-proteobacteria, even more preferred enterobacteria; and/or deferribacteres in the gut is selected from the group consisting of bacterial phages, prebiotics, food grade bacteria, in particular probiotics, yeasts, phytochemicals, antibiotics and mixtures thereof.

In the case of bacterial phages it is preferred that the phages are food grade phages. In particular T4 phages, such as ED6, and T7 phages can be successfully applied in the framework of the present invention. Phages have the advantage that they are very specific to targeted bacteria and very stable even after long storage times without losing biological activities. The heat stability of phages makes them suitable for food products that are heated during the production process or during preparation prior to consumption. Furthermore, phages are stable in a number of different media, including the stomach and gut media.

Prebiotics may be dietary fibers. Dietary fibers may be selected from the group consisting of fructo-oligosaccharides, galacto-oligosaccharides, xylo-oligosaccharides, isomalto-saccharides, soya oligosaccharides, pyrodextrins, transgalactosylated oligosaccharides, lactulose, beta-glucan, insulin, raffinose, stachyose. Dietary fibers also have the advantage of being resistant to a number of conditions including heating and long storage times. They furthermore may contribute to a treatment in the framework of the present invention by improving gastrointestinal health and by increasing satiety.

Food grade bacteria are preferably probiotic bacteria and may be selected from the group consisting of *Bifidobacterium, Lactobacillus, Lactococcus, Enterococcus, Streptococcus Ascomycota, Deuteromycota, Debaryomyces, Kluyveromyces, Saccharoymces, Yarrowia, Zygosaccharomyces, Candida,* and *Rhodotorula*; preferentially lactic acid bacteria and bifidobacteria, or mixtures thereof; and/or in particular may be selected from the group consisting of *Bifidobacterium longum, Bifidobacterium lactis, Bifidobacterium animalis, Bifidobacterium breve, Bifidobacterium infantis, Lactobacillus acidophilus, Lactobacillus casei, Lactobacillus salivarius, Lactococcus lactis, Lactobacillus reuteri, Lactobacillus rhamnosus, Lactobacillus paracasei, Lactobacillus johnsonii, Lactobacillus plantarum, Lactobacillus salivarius, Enterococcus faecium, Saccharomyces cerevisia, Saccharomyces boulardii* and *Lactobacillus reuteri* or mixtures thereof, preferably selected from the group consisting of *Lactobacillus johnsonii* (NCC533; CNCM I-1225), *Bifidobacterium longum* (NCC490; CNCM I-2170), *Bifidobacterium longum* (NCC2705; CNCM I-2618), *Bifidobacterium lactis* (2818; CNCM 1-3446), *Lactobacillus paracasei* (NCC2461; CNCM I-2116), *Lactobacillus rhamnosus* GG (ATCC53103), *Lactobacillus rhamnosus* (NCC4007; CGMCC 1.3724), deposited in October 2004 at the China General Microbiological Culture Collection Center, Chinese Academy of Sciences, P.O. Box 2714, Beijing, China 100080, *Enterococcus faecium* SF 68 (NCIMB10415), and mixtures thereof.

Yeasts are preferably food grade yeasts and may be selected from the group consisting of *saccharomyces boulardii* and *saccharomyces cerevisiae* or mixtures thereof. Food grade bacteria, in particular probiotic bacteria and food grade yeasts have the advantage that they may additionally confer benefits to the patient, in particular to the intestinal flora of the patient. These additional benefits are generally known to those skilled in the art and may include managing lactose intolerance, prevention of colon cancer, lowering cholesterol, lowering blood pressure, improving immune function and preventing infections, reducing inflammation and/or improving mineral absorption.

Antibiotics may be selected from the group consisting of a class of aminoglycoside antibiotics such as neomycin, kanamycin, streptomycin, a class of polypeptide antibiotics such as polymyxin B, a class of penicillin beta-lactam such as ampicillin and a class of quinolone/fluoroquinolone antibiotics such as ciprofloxacin and norfloxacin. Using antibiotics has the advantage that their dosing can be determined with high accuracy. Furthermore, usually only very small quantities are required to achieve an effect, so that antibiotics are in particular useful for applications in medicaments.

The agent capable of reducing the amount of proteobacteria, preferably gamma-proteobacteria, even more preferred enterobacteria; and/or deferribacteres in the gut may also be a phytochemical, in particular a phytonutrient. Phytochemicals are plant or fruit derived chemical compounds. "Phytonutrients" refer to phytochemicals derived from edible plants. Using phytonutrients and or phytochemicals has the advantage that the effect of the present invention can be achieved with natural foods or extracts from natural foods without having to add synthesized compounds to the composition prepared by the use of the present invention. In the framework of the present invention the phytochemicals may be selected from the group consisting of phytochemicals from green tea or coffee such as indole, polyphenols, such as epigallocatechin and epigallocatechin gallate or the polymers of such, phytochemicals from black tea such as theaflavin or theaflavin mixtures, tennic acid, procyanidin, phytochemicals from cashew apple flavour such as (E)-2-hexenal, phytochemicals from rosemary, such as carnosol, carnosic acid or rosmarinic acid, or mixtures thereof.

The primary composition may further comprise a pharmaceutically acceptable carrier. Applicable pharmaceutically acceptable carriers are known to those of skill in the art. The pharmaceutically acceptable carrier may be any carrier known in the field as suitable for pharmaceutical and/or oral application. Suitable pharmaceutical carriers and formulations may include sugars and starches. Additional examples of pharmaceutically acceptable carriers are described, for example, in Remington's Pharmaceutical Sciences (19th ed.) (Genarro, ed. (1995) Mack Publishing Co., Easton, Pa.), the contents of which is herewith incorporated herein by reference. The addition of a carrier has the advantage that the agent capable of reducing the amount of proteobacteria, preferably gamma-proteobacteria, even more preferred enterobacteria; and/or deferribacteres in the gut is further stabilized for long storage times. Furthermore, exact dosing is facilitated.

The composition prepared by the use of the present invention may also be formulated as sustained release formulation. This way an increased bioavailability and effectiveness of the agent capable of reducing the amount of enterobacteria in the gut can be achieved.

Generally, the dosage of the agent capable of reducing the amount of proteobacteria, preferably gamma-proteobacteria, even more preferred enterobacteria; and/or deferribacteres in the gut can be adjusted by those skilled in the art to the designated purpose. Any dose showing an effect is suitable. However, e.g., for probiotic bacteria it is preferred that the composition comprises between $10^2$ and $10^{12}$ cells of probiotic per g of the dry weight of the composition. Importantly, for the effectiveness of the agent capable of reducing the amount of enterobacteria in the gut it is not necessarily required that the probiotic bacteria are alive in the composition. The probiotics might also be effective, e.g., by means of their metabolites that they have produced. Using inactive probiotics has the advantage that the amount of active agent can be exactly determined. Furthermore, inactive probiotics are usually very storage stable and easy to incorporate in products.

However, it is preferred if the probiotics are alive, since in this case they may be able to colonize the intestine and increase their effectiveness through colonization. Consequently, in a preferred embodiment of the present invention the composition comprises between $10^2$ and $10^{12}$ cfu of probiotic per g of the dry weight of the composition.

The daily dose of probiotics in the composition will depend on the particular person or animal to be treated. Important factors to be considered include age, body weight, sex and health condition. For example a typical daily dose of probiotic in the composition described in the present invention will be in the range of $10^4$-$10^{12}$ cfu and/or cells per day, preferably $10^6$-$10^{10}$ cfu and/or cells per day, preferably $10^7$-$10^9$ cfu and/or cells per day.

Similarly, it is preferred that the composition comprises between $10^2$ and $10^{12}$ pfu of phages per g of the dry weight.

The composition may also comprise between 1μg-500 mg prebiotics per g of the dry weight.

In a further embodiment the composition may comprise between 1 μg-100 mg antibiotics per g of the dry weight.

In another embodiment the composition may comprise between 1 μg-500 mg phytochemicals per g of the dry weight.

If the composition that is prepared by the use of the present invention is a liquid, in particular a drink, the given amounts should be understood as per g of the final product instead of per g of dry weight.

Of course, the agents capable of reducing the amount of proteobacteria, preferably gamma-proteobacteria, even more preferred enterobacteria; and/or deferribacteres in the gut may be combined.

Typical food products that may be prepared in the framework of the present invention may be selected from the group consisting of: milk-powder based products; instant drinks; ready-to-drink formulations; nutritional powders; milk-based products, in particular yoghurts or ice cream; cereal products; beverages; water; coffee; cappuccino; malt drinks; chocolate flavoured drinks; culinary products and soups.

The composition of the present invention may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. The composition may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. In all cases, such further components will be selected having regard to their suitability for the intended recipient.

The composition may be a nutritionally complete formula.

The composition according to the invention may comprise a source of protein.

Any suitable dietary protein may be used, for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred.

The proteins may be intact or hydrolysed or a mixture of intact and hydrolysed proteins. It may be desirable to supply partially hydrolysed proteins (degree of hydrolysis between 2 and 20%), for example for animals believed to be at risk of developing cows' milk allergy. If hydrolysed proteins are required, the hydrolysis process may be carried out as desired and as is known in the art. For example, a whey protein hydrolysate may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

The composition may also contain a source of carbohydrates and a source of fat.

If the composition includes a fat source, the fat source preferably provides 5% to 40% of the energy of the composition; for example 20% to 30% of the energy. A suitable fat profile may be obtained using a blend of canola oil, corn oil and high-oleic acid sunflower oil.

A source of carbohydrate may be added to the composition.

The source of carbohydrates preferably provides 40% to 80% of the energy of the composition. Any suitable carbohydrate may be used, for example sucrose, lactose, glucose, fructose, corn syrup solids, maltodextrins, and mixtures thereof. Dietary fibre may also be added if desired. Dietary fibre passes through the small intestine undigested by enzymes and functions as a natural bulking agent and laxative. Dietary fibre may be soluble or insoluble and in general a blend of the two types is preferred. Suitable sources of dietary fibre include soy, pea, oat, pectin, guar gum, gum Arabic, fructooligosaccharides, galacto-oligosaccharides, sialyl-lactose and oligosaccharides derived from animal milks. A preferred fibre blend is a mixture of insulin with shorter chain facto-oligosaccharides. Preferably, if fibre is present, the fibre content is between 2 and 40 g/l of the composition as consumed, more preferably between 4 and 10 g/l.

The composition may also contain minerals and micronutrients such as trace elements and vitamins in accordance with the recommendations of Government bodies such as the USRDA. For example, the composition may contain per daily dose one or more of the following micronutrients in the ranges given:—300 to 500 mg calcium, 50 to 100 mg magnesium, 150 to 250 mg phosphorus, 5 to 20 mg iron, 1 to 7 mg zinc, 0.1 to 0.3 mg copper, 50 to 200 µg iodine, 5 to 15 µg selenium, 1000 to 3000 µg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 µg Vitamin B12, 100 to 800 µg folic acid, 30 to 70 µg biotin, 1 to 5 µg Vitamin D, 3 to 10 µg Vitamin E.

One or more food grade emulsifiers may be incorporated into the composition if desired; for example diacetyl tartaric acid esters of mono- and di-glycerides, lecithin and mono- and di-glycerides. Similarly suitable salts and stabilisers may be included.

The composition is preferably orally or enterally administrable; for example in the form of a powder for re-constitution with milk or water.

Preferably, the composition is provided in the form of a powder, e.g., a shelf stable powder. Shelf stability can be obtained, for example by providing the composition with a water activity smaller than 0.2, for example in the range of 0.19-0.05, preferably smaller than 0.15.

Water activity or $a_w$ is a measurement of the energy status of the water in a system. It is defined as the vapor pressure of water divided by that of pure water at the same temperature; therefore, pure distilled water has a water activity of exactly one.

The composition described above may be prepared in any suitable manner. For example, it may be prepared by blending together the protein, the carbohydrate source, and the fat source in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture is then homogenised; for example in two stages.

The liquid mixture may then be thermally treated to reduce bacterial loads, by rapidly heating the liquid mixture to a temperature in the range of about 80° C. to about 150° C. for about 5 seconds to about 5 minutes, for example. This may be carried out by steam injection, autoclave or by heat exchanger; for example a plate heat exchanger.

Then, the liquid mixture may be cooled to about 60° C. to about 85° C.; for example by flash cooling. The liquid mixture may then be again homogenised; for example in two stages at about 10 MPa to about 30 MPa in the first stage and about 2 MPa to about 10 MPa in the second stage. The homogenised mixture may then be further cooled to add any heat sensitive components; such as vitamins and minerals. The pH and solids content of the homogenised mixture are conveniently adjusted at this point.

The homogenised mixture is transferred to a suitable drying apparatus such as a spray drier or freeze drier and converted to powder. The powder should have a moisture content of less than about 5% by weight.

For example then the agent that reduces the amount of enterobacteria in the gut may be added in appropriate amounts. Depending on the kind of agent that reduces the amount of enterobacteria the agent may also be added at an earlier stage.

It is clear to those skilled in the art that they can freely combine features described in this disclosure without departing from the scope of the invention as originally disclosed.

Further advantages and features of the present invention will be apparent to those of skill in the art from the following examples and figures.

Figure 5:
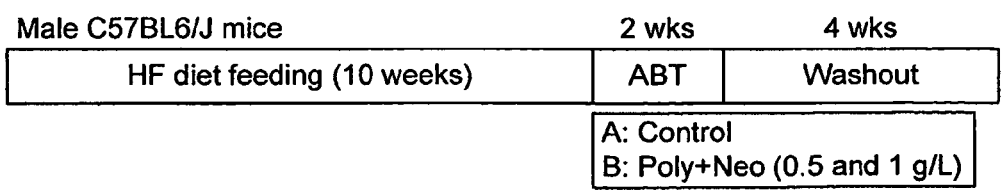

FIG. 5 shows the study design for gut microbiota modulation by polymyxin B and neomycin. High fat diet induced obese and insulin resistant C57BL/6J mice were randomized to two groups. One group received a placebo treatment (n=24) and the other group received polymyxin B and neomycin in the drinking water (n=24). A half of mice in each group were sacrificed immediately after the termination of the treatment (n=12/group). The remaining mice were sacrificed after a 4-week washout period (n=12/group).

Figure 6:
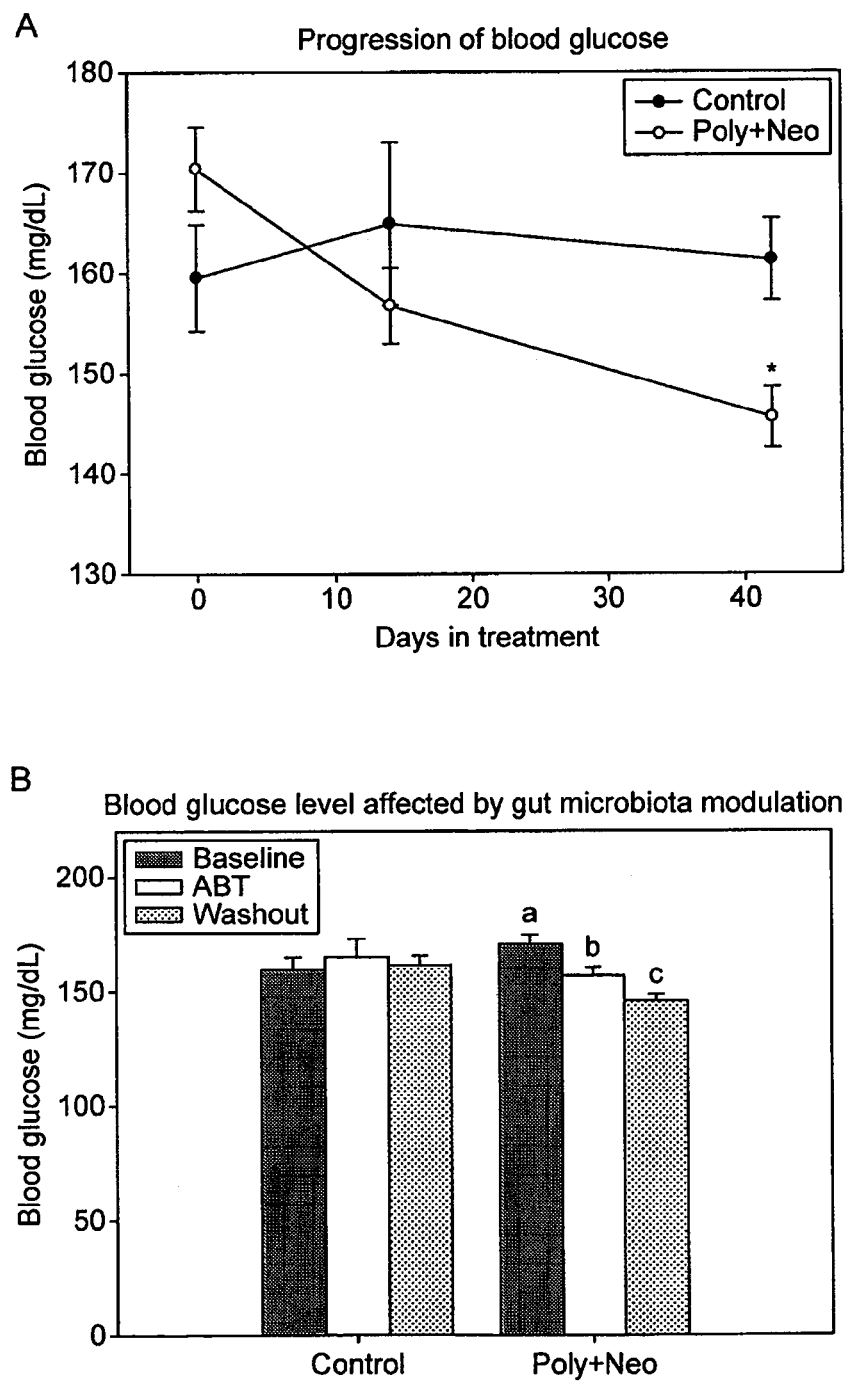

FIG. 6 shows the modulation of gut microbiota reduced blood glucose concentrations in insulin resistant mice. Blood glucose concentrations were measured in mice under 6 hour food restriction in the light cycle (8:00 to 14:00). Changes in blood glucose concentrations were expressed in a line graph (A) and in a bar graph (B). Data are median±semedian, n=12. Kruskal-Wallis test followed by Wilcoxon tests for pair-wise comparisons were applied. A different letter or * indicates $p<0.05$.

Figure 7:
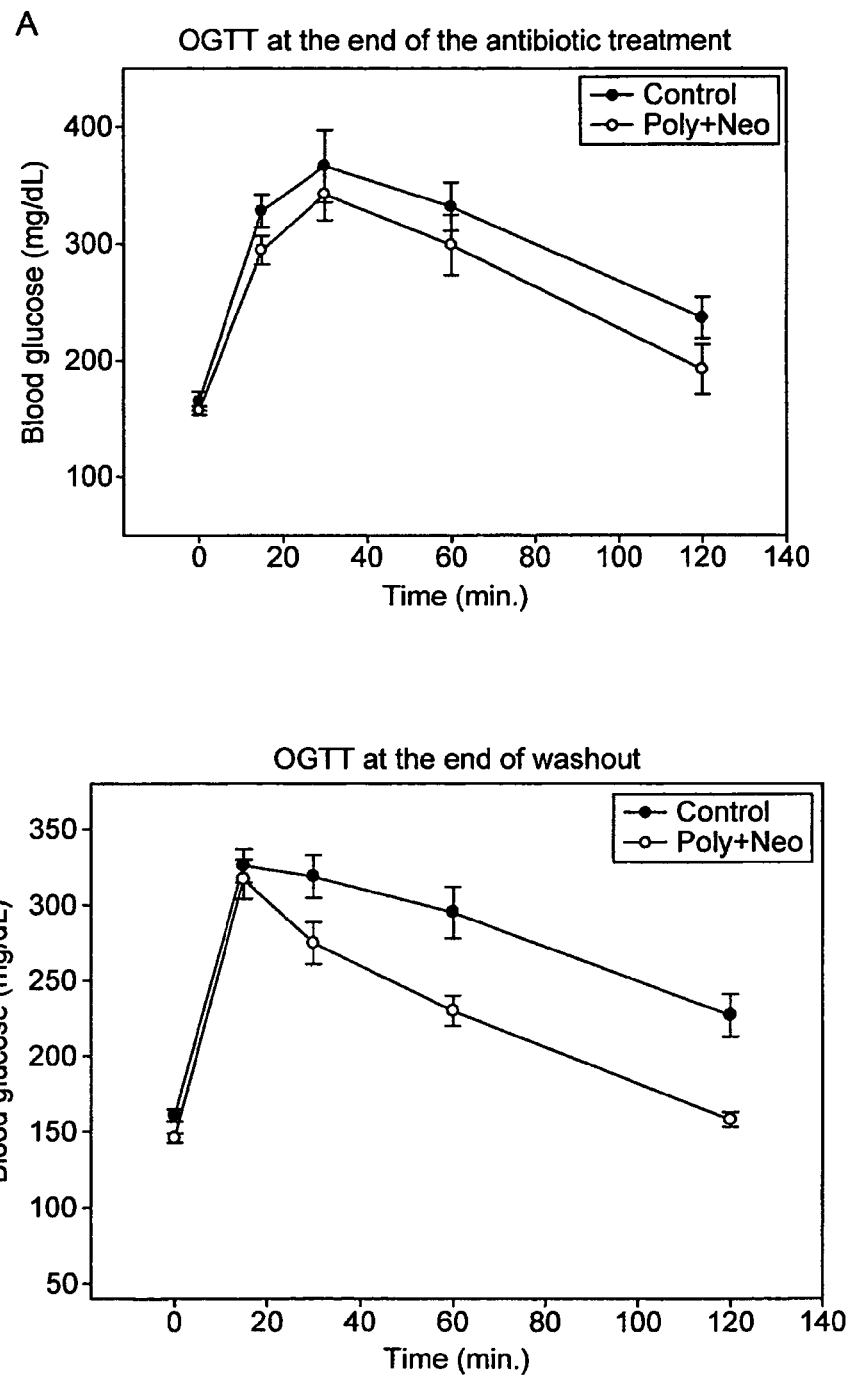

FIG. 7 shows the oral glucose tolerance of DIO mice treated with placebo or a combination of polymyxin B and neomycin. Results of blood glucose excursion during the OGTT were shown. Mice were tested at the end of antibiotic treatment period (A) and the end of washout period (B). Data are median±semedian, n=12.

Figure 8:
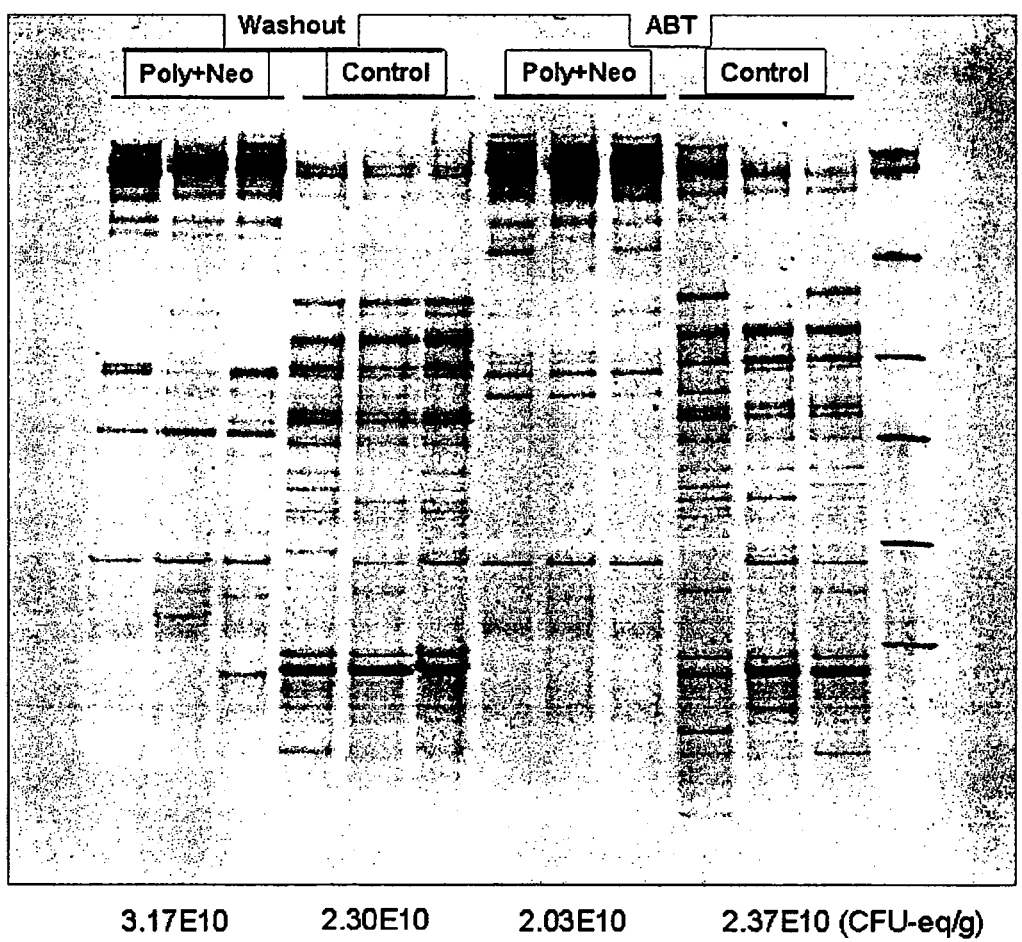

FIG. 8 shows the composition of cecal microbiota analyzed by DGGE technique. ABT represents the samples collected at the end of antibiotic treatment period. Washout represents the sample collected at the end of washout period. Numbers on the bottom of the gel indicate the total number of bacteria. The bacteria number was determined by a quantitative PCR technique, and the results were expressed as CFU-equivalent per gram of cecal content.

Figure 9:
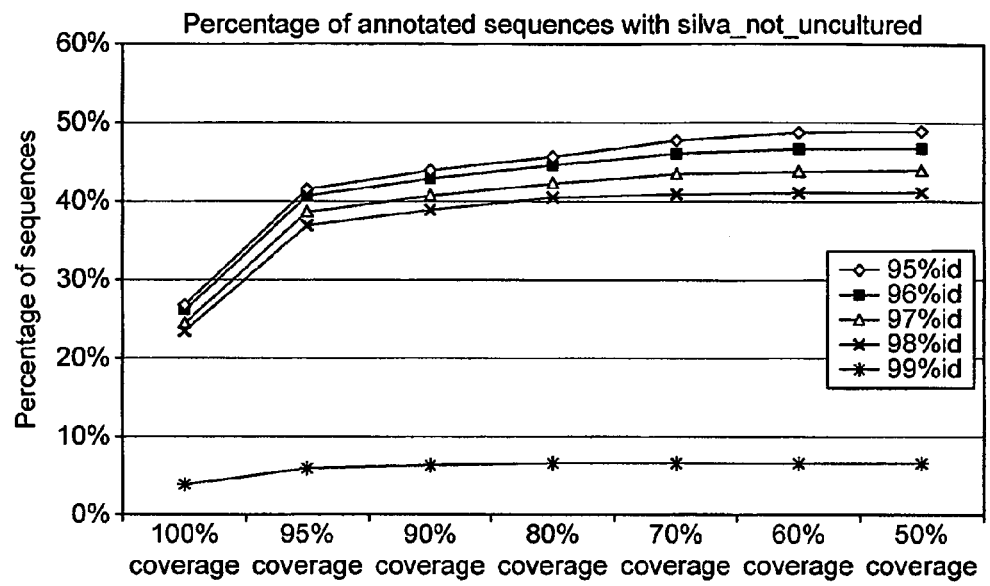

FIG. 9 shows the percentage of annotated 16S sequences from the 8 libraries for various identity thresholds when varying the percent query coverage. Annotation was made searching against the Silva database subdivision curated from unidentified 16S sequences.

Figure 10:
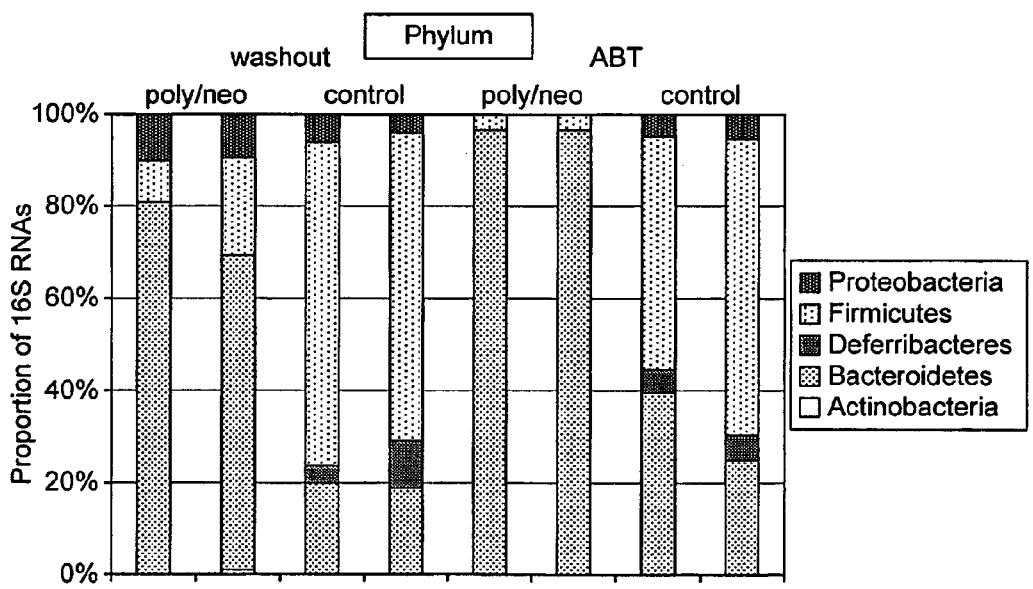

FIG. 10 shows the 16S classification at the phylum level using RDP-II Classifier.

Figure 11:
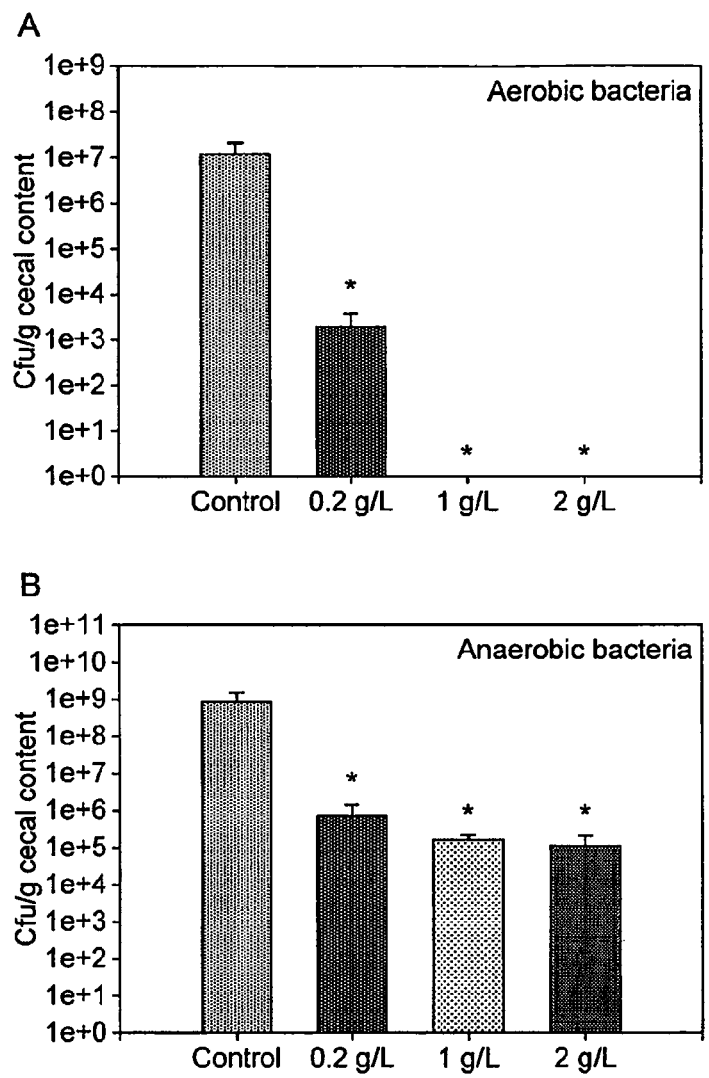

FIG. 11 shows the effect of gut microbiota reduction on cecal bacteria in ob/ob mice. Cecal samples were cultured in aerobic (A) and anaerobic (B) environment. Aerobic bacteria counts went below the detection limit in the groups treated with the combination of norfloxacin and ampicillin at 1 and 2 g/L. Data are median±semedian, n=6.*$p<0.05$ vs control.

Figure 12:
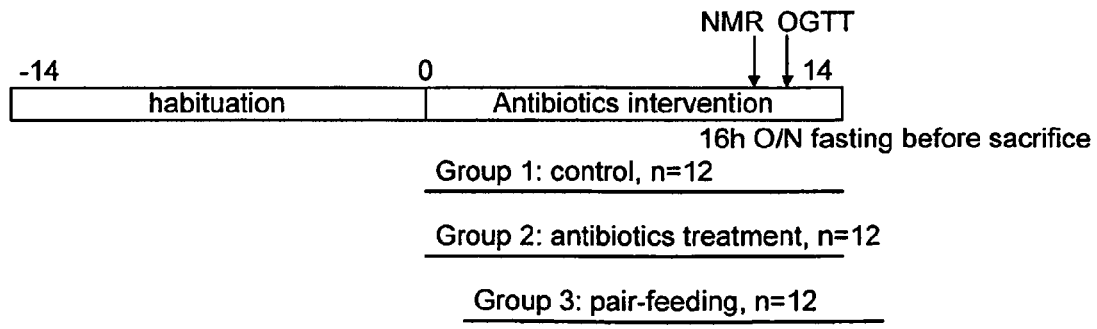

FIG. 12 shows the design of a study. Twelve ob/ob mice were randomized into one of three experimental groups. The group one was treated with placebo. The group two received oral antibiotic treatment with norfloxacin and ampicillin in the drinking water. The group three had controlled feeding and ate the same amount of food as the group two.

Figure 13:
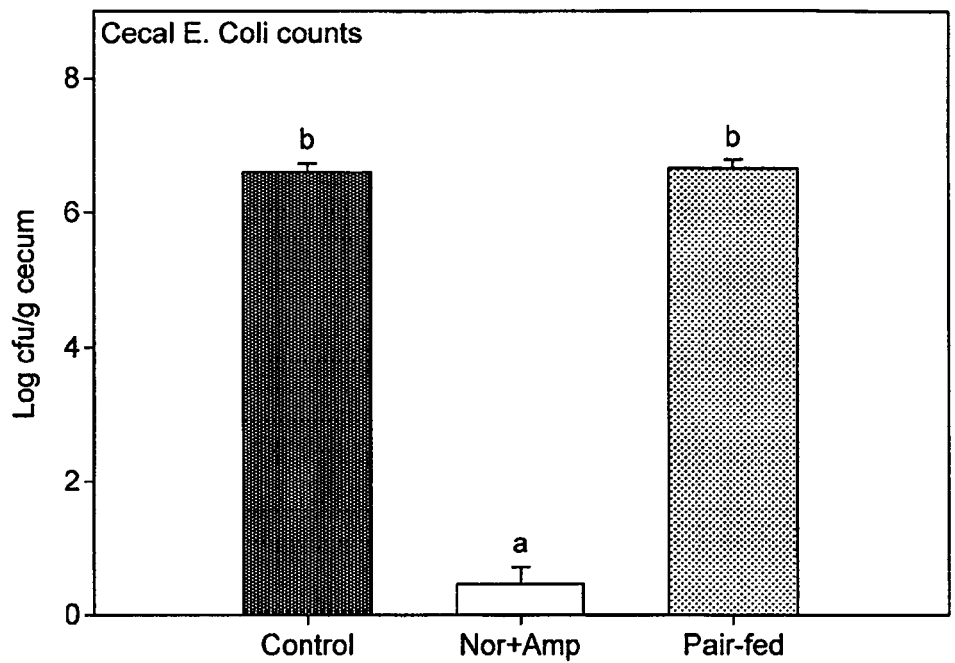
Figure 13:
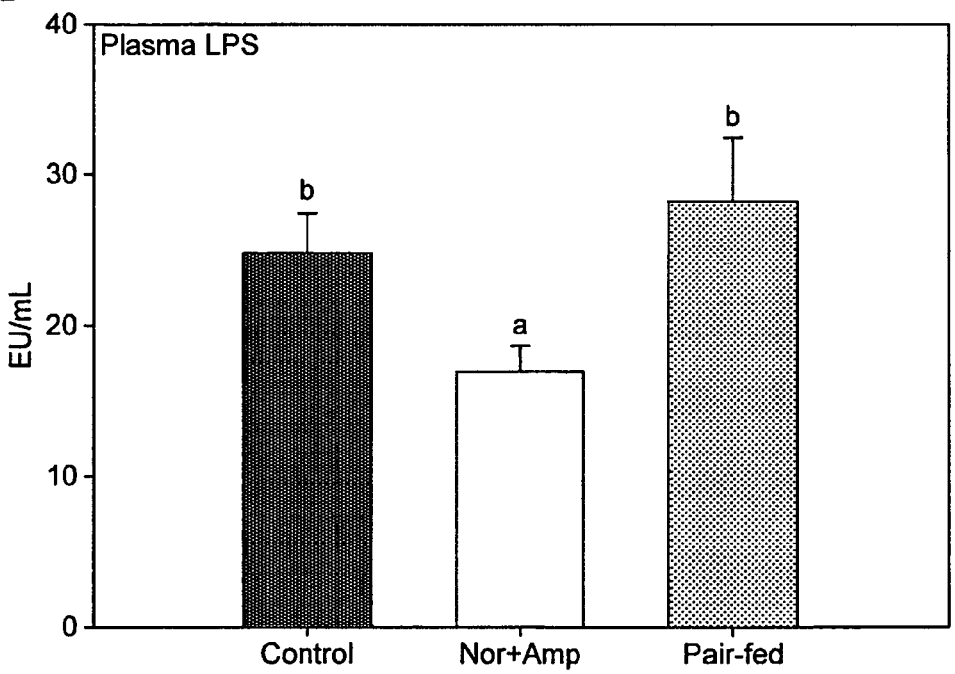

FIG. 13 shows the reduction of cecal enterobacteria and Gram negative bacteria specific lipopolysaccharide (LPS). Cecal contents were collected and plated in Mueller Hinton agar, a culture condition specific for growing enterobacteria (A). Plasma lipopolysaccharide concentrations were determined using a kit based on Limulus amoebocyte extract (LAL kit; Cambrex BioScience, Walkersville). Data are median±semedian, n=12. Kruskal-Wallis test followed by Wilcoxon tests for pair-wise comparisons were applied. Different letters indicate statistical significance $p<0.05$.

Figure 14:
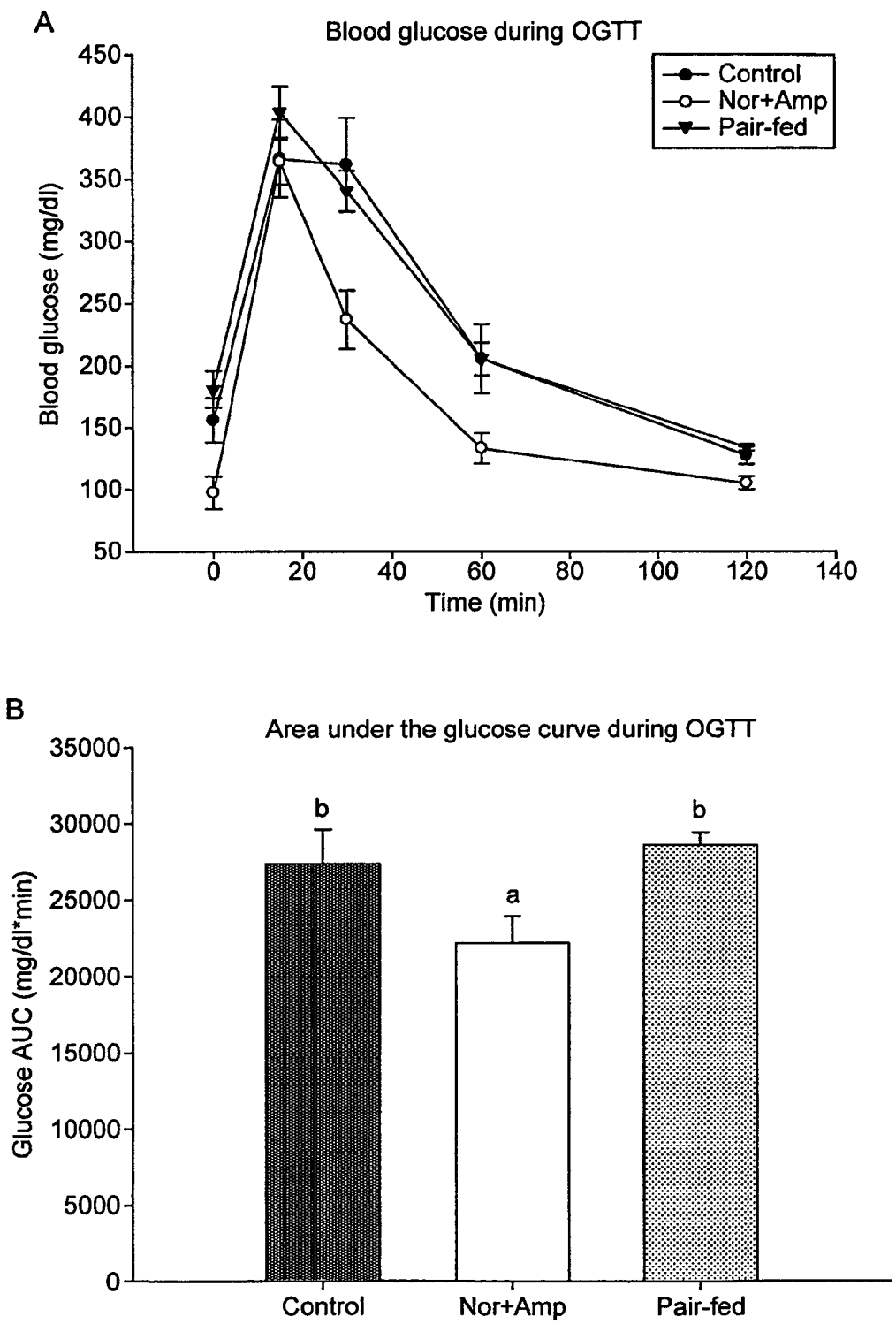
Figure 15:
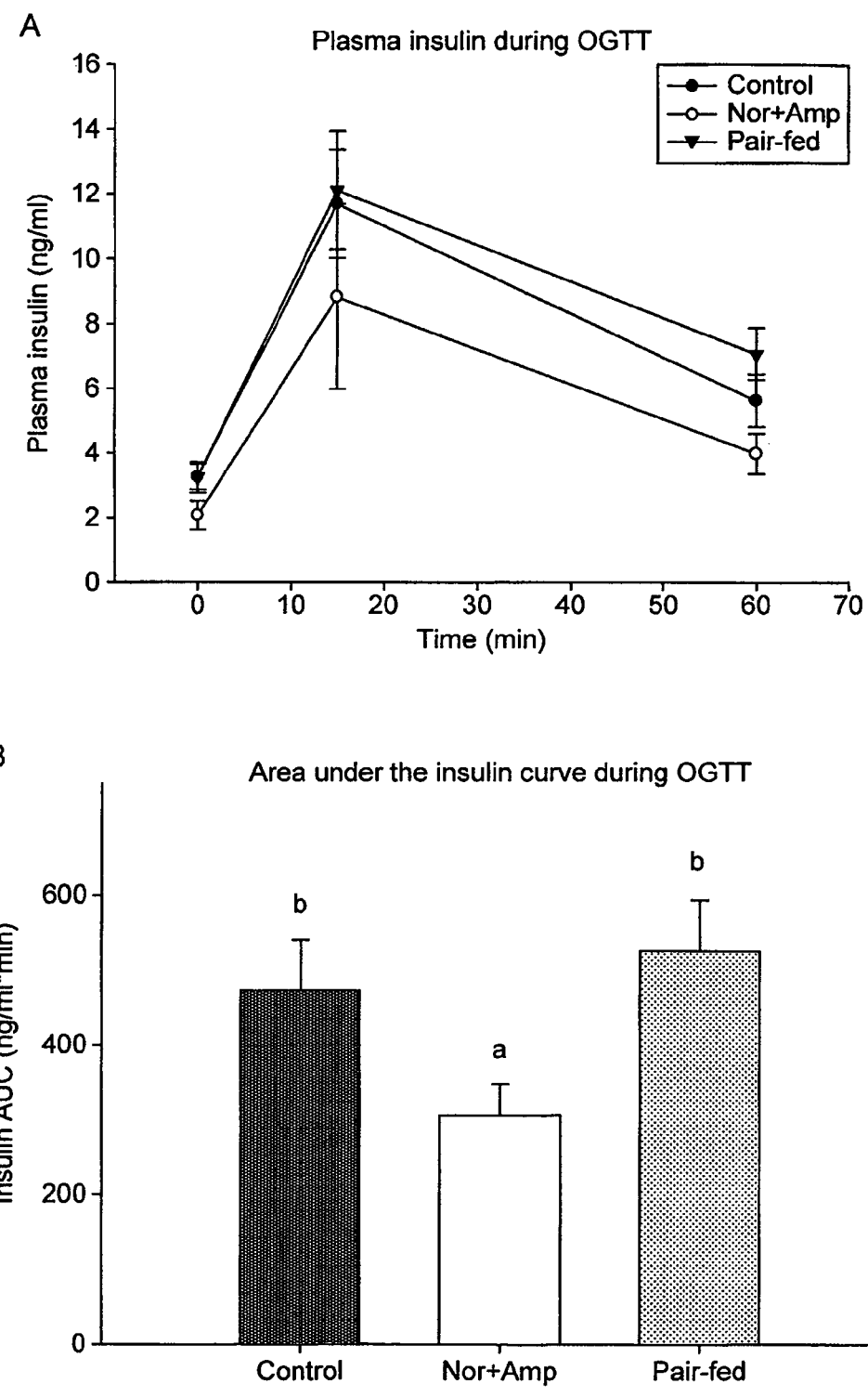
Figure 16:
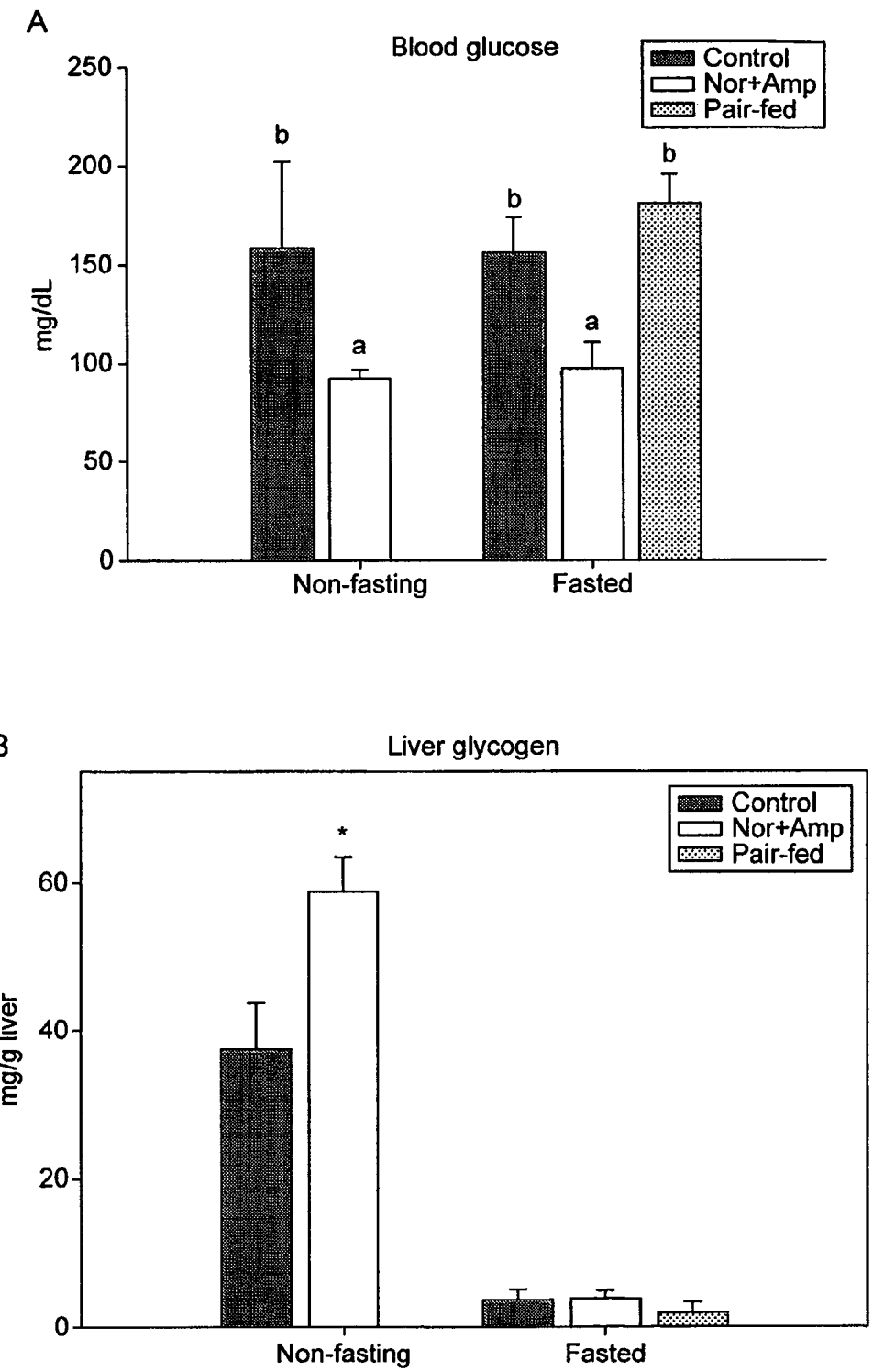

FIG. 14 shows the gut microbiota reduction improved oral glucose tolerance of ob/ob mice. Results of blood glucose (A) and the area under glucose curves (B) during oral glucose tolerance tests in ob/ob mice. All mice were fasted overnight (15 h) before the OGTT. Data are median±semedian, n=12. Kruskal-Wallis test followed by Wilcoxon tests for pair-wise comparisons were applied. Different letters indicate statistical significant $p<0.05$ FIG. 15 shows the gut microbiota reduction decreased insulin secretion during the oral glucose tolerance test of ob/ob mice. The plasma insulin concentrations at OGTT are illustrated (A) and the area under the insulin curves (B) during the OGTT. Data are median±semedian, n=12. Kruskal-Wallis test followed by Wilcoxon tests for pair-wise comparisons were applied. Different letters indicate statistical significant $p<0.05$ FIG. 16 shows the improvement of glycemic control in the diabetic ob/ob mice receiving gut microbiota reduction treatment. Blood glucose concentrations (A) and liver glycogen levels (B) in the fasting and non-fasting state are illustrated. Data are median±semedian, n=12 for the fasted; n=6 for the non-fasting. Kruskal-Wallis test followed by Wilcoxon tests for pair-wise comparisons were applied. * or a different letter indicates statistical significance $p<0.05$.

Figure 17:
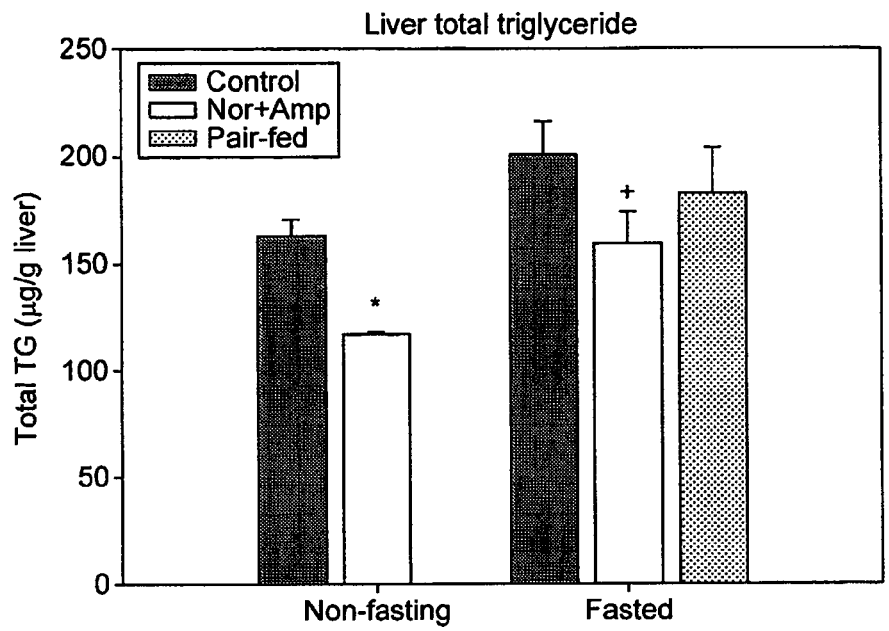

FIG. 17 shows the gut microbiota reduction by norfloxacin and ampicillin ameliorated liver triglyceride accumulation. Liver triglycerides at the fasting and non-fasting state were illustrated. Data are median±semedian, n=12 for the fasted; n=6 for the non-fasting. Kruskal-Wallis test followed by Wilcoxon tests for pair-wise comparisons were applied. * indicates statistical significance $p<0.05$; + indicates statistical trend $0.1<p<0.05$.

Figure 18:
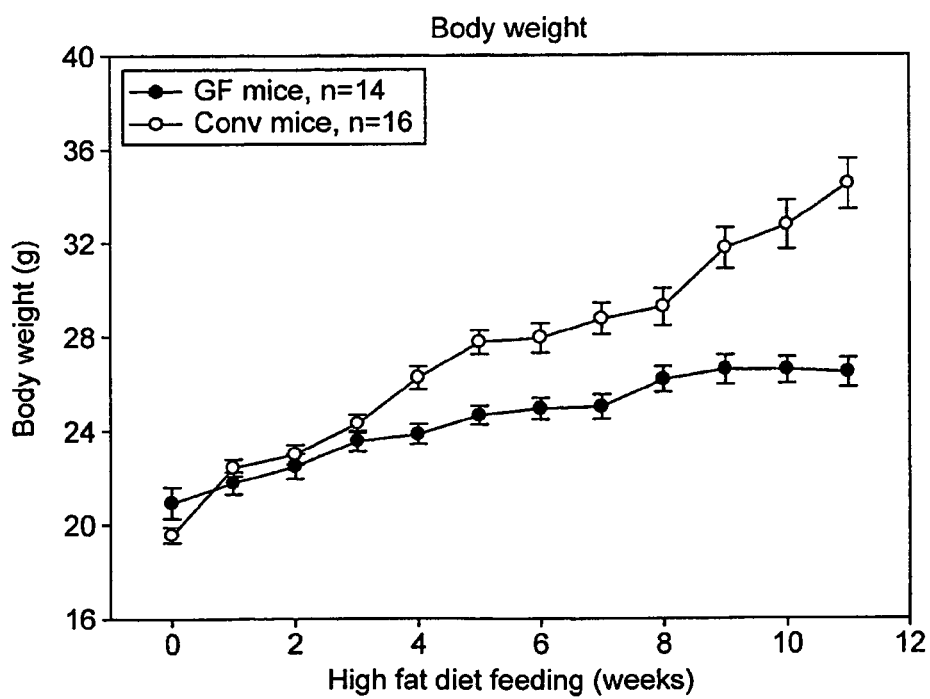

FIG. 18 shows the body weight gain of germ free and conventional C57BL/6J mice when eating a sterile high fat diet. Body weights of the mice were measured once a week for 11 weeks. Data are mean±sem, n=14 for germ free mice; n=16 for conventional mice.

Figure 19:
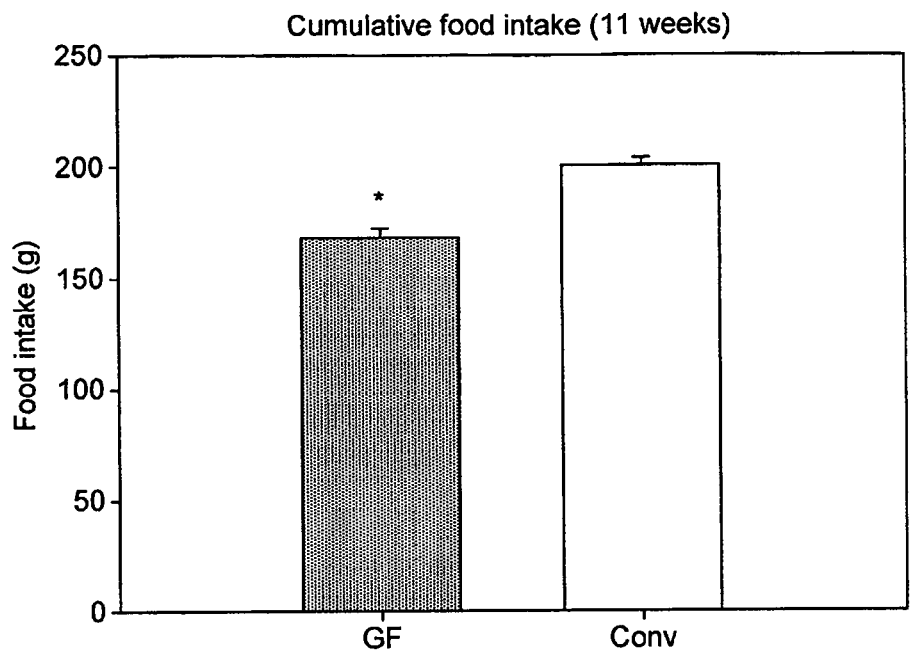
Figure 20:
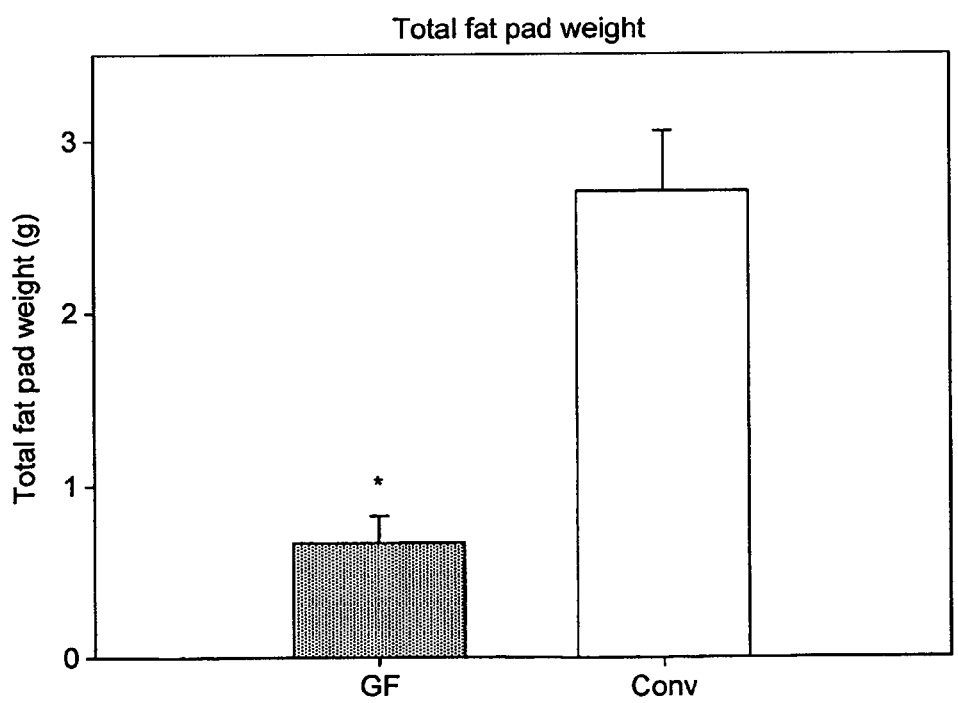
Figure 21:
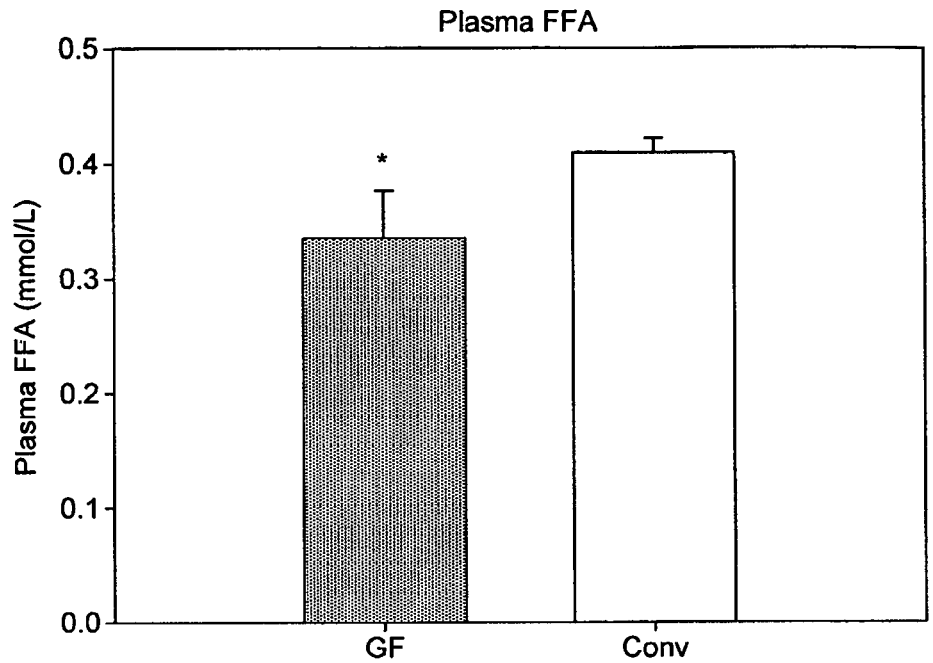
Figure 22:
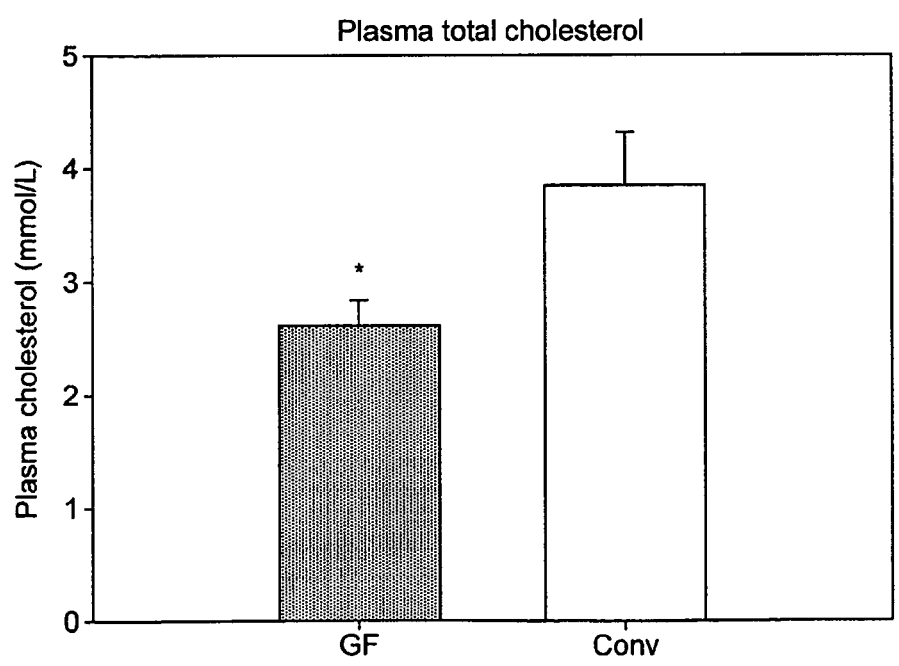
Figure 23:
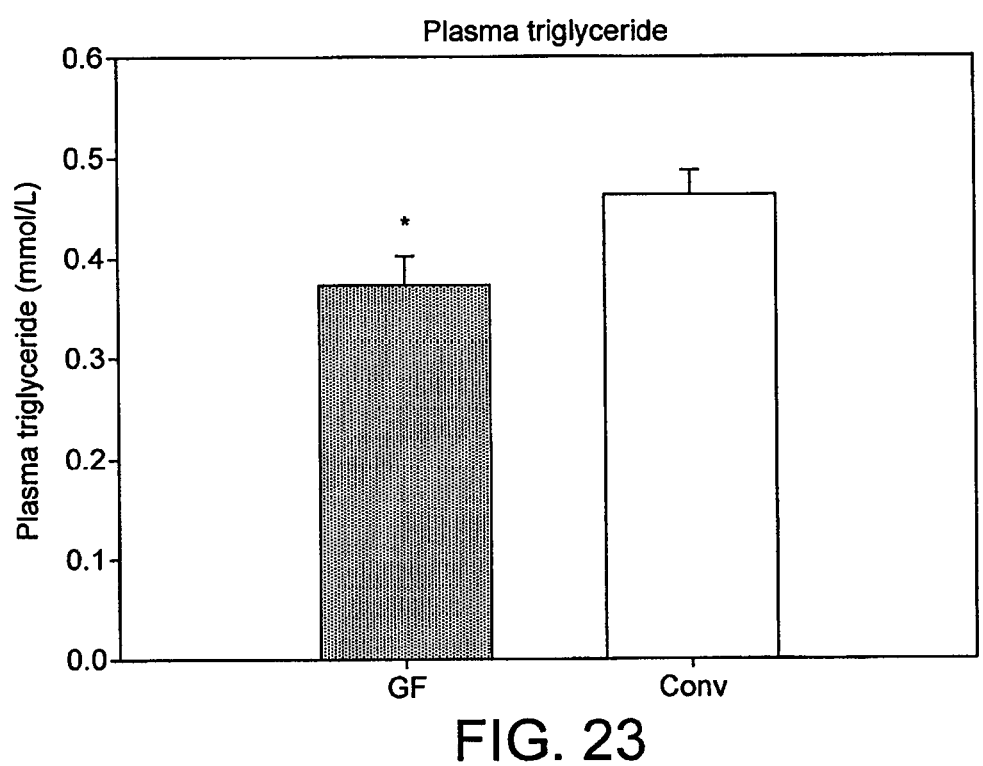
Figure 24:
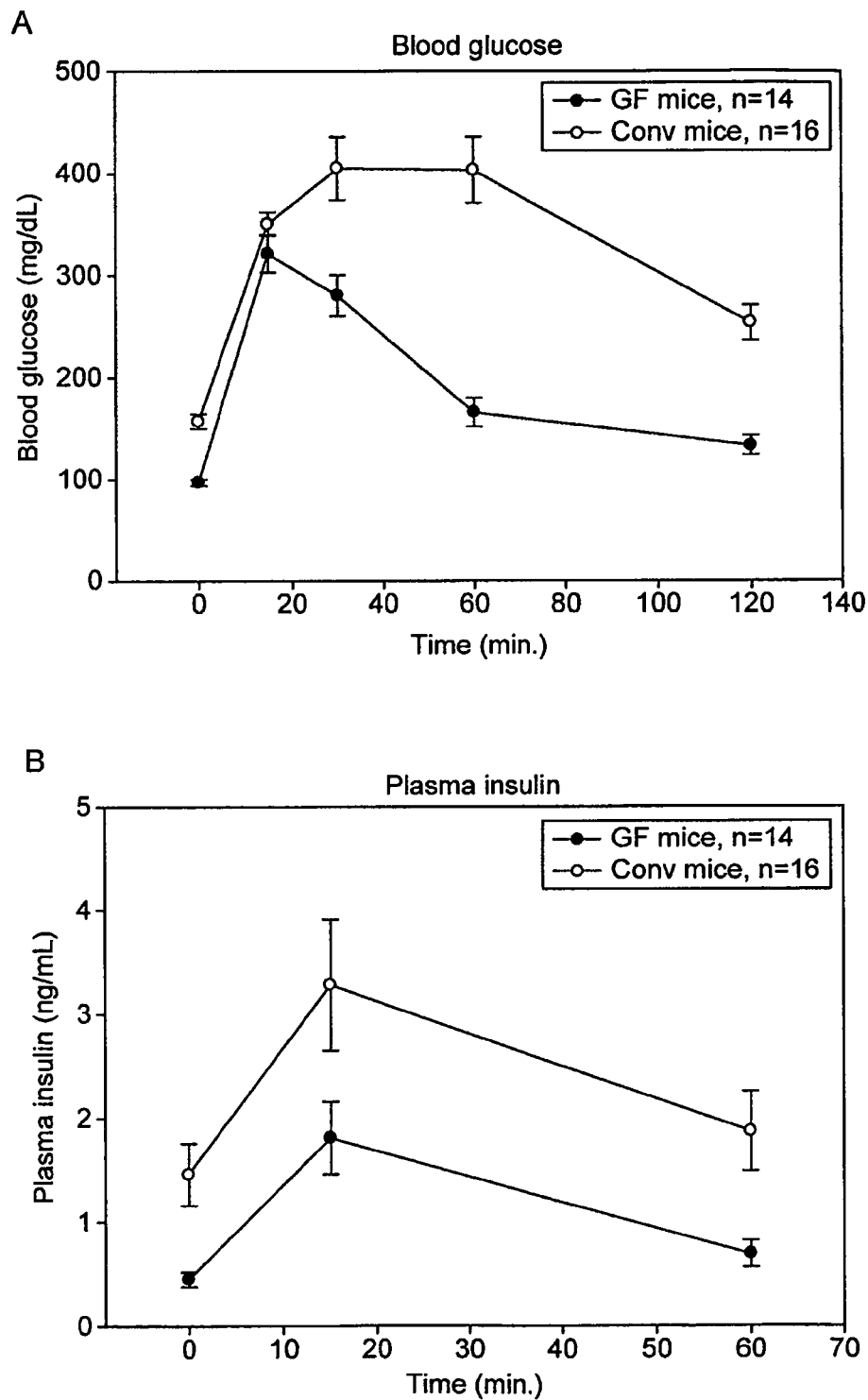

FIG. 19 shows the cumulative food intake of germ free and conventional mice when eating a high fat diet. Food intake was measured once a week for 11 weeks. Data are median±semedian, n=14 for germ free mice; n=16 for conventional mice. Kruskal-Wallis test followed by Wilcoxon tests for pair-wise comparisons were applied. * $p<0.05$ vs conventional mice FIG. 20 shows the total fat pad weight in germ free and conventional C56BL/6J mice. Total fat pad includes epididymal, mesenteric and retroperitoneal fat pads. Data are median±semedian, n=14 for germ free mice; n=16 for conventional mice. Kruskal-Wallis test followed by Wilcoxon tests for pair-wise comparisons were applied. * $p<0.05$ vs conventional mice FIG. 21 shows the plasma free fatty acid levels in the germ free and conventional mice. Blood samples collected during the sacrifice were used for the analysis of plasma free fatty acids. Data are median±semedian, n=9-11. Kruskal-Wallis test followed by Wilcoxon tests for pair-wise comparisons were applied. * $p<0.05$ vs conventional mice FIG. 22 shows the plasma total cholesterol levels in the germ free and conventional mice. Blood samples collected during the sacrifice were used for the analysis of plasma total cholesterol. Data are median±semedian, n=9-11. Kruskal- Wallis test followed by Wilcoxon tests for pair-wise comparisons were applied. * p<0.05 vs conventional mice FIG. 23 shows the plasma triglyceride levels in the germ free and conventional mice. Blood samples collected during the sacrifice were used for the analysis of plasma triglycerides. Data are median±semedian, n=9-11. Kruskal-Wallis test followed by Wilcoxon tests for pair-wise comparisons were applied. * p<0.05 vs conventional mice FIG. 24 shows the oral glucose tolerance of germ free and conventional on a high fat diet. Six hour food deprivation was applied to all mice before OGTTs. Germ free mice were taken out of an isolator prior to the OGTTs and OGTTs were done in a conventional laboratory. Data are median±semedian, n=14 for germ free mice; n=16 for conventional mice.

Figure 25:
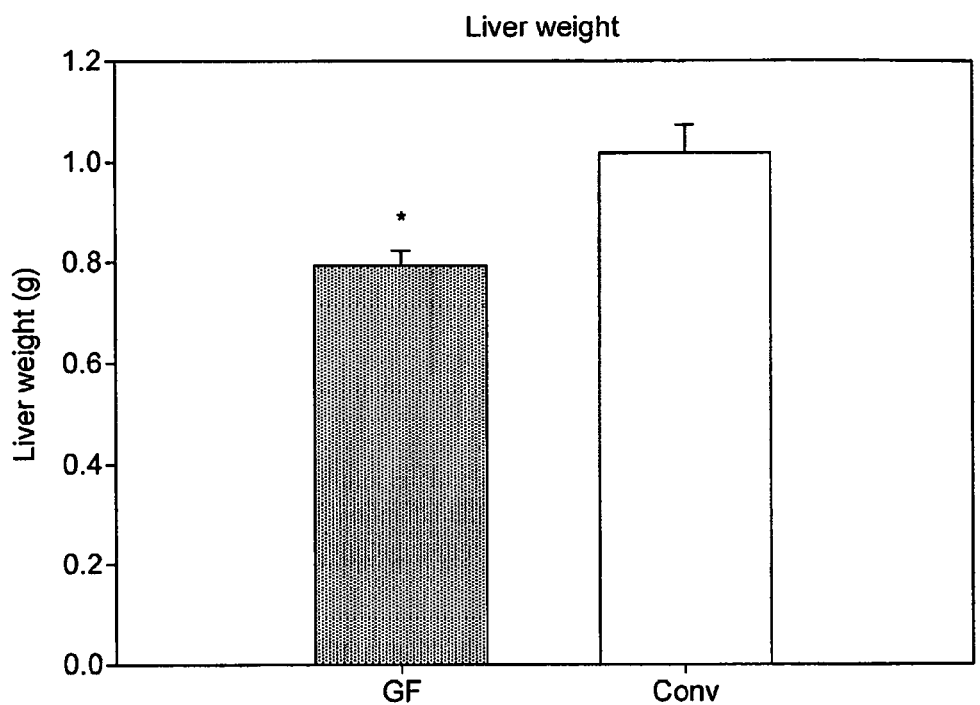

FIG. 25 shows the liver weight of germ free and conventional DIO mice.

Figure 26:
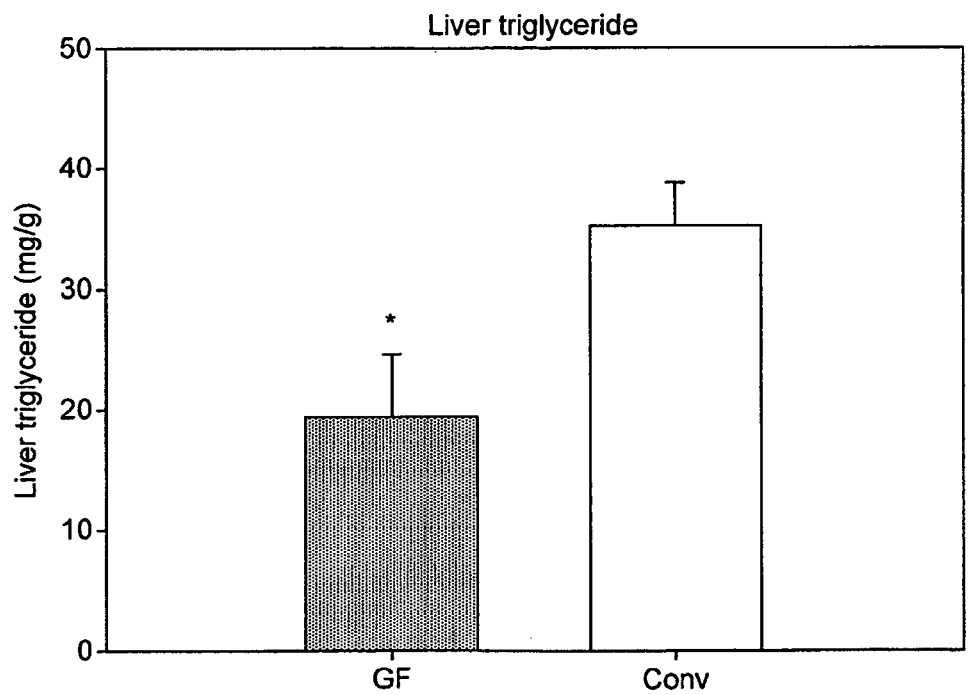
Figure 27:
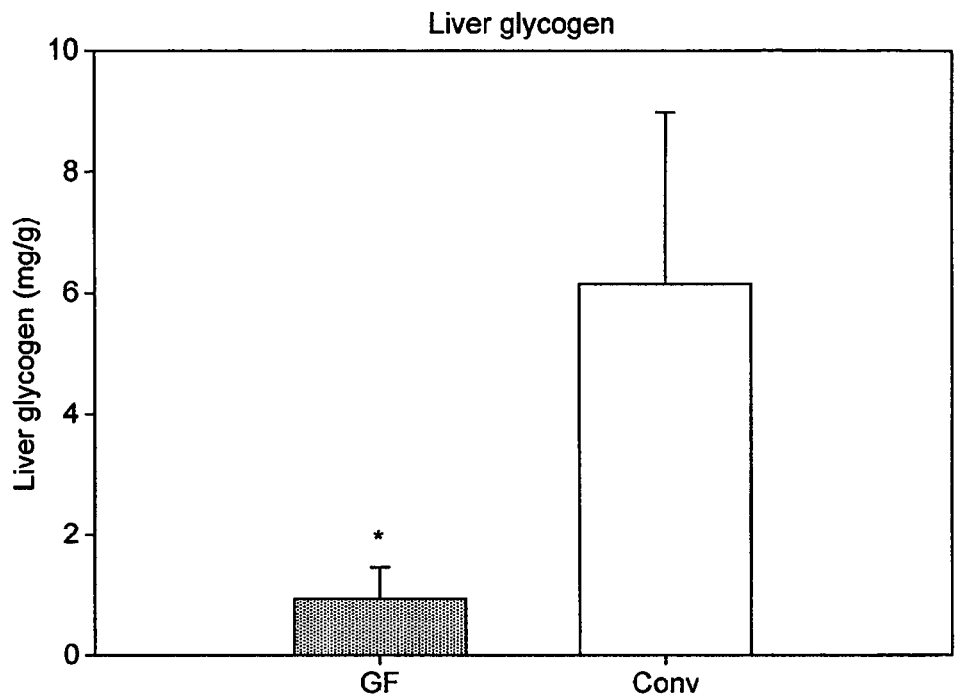
Figure 28:
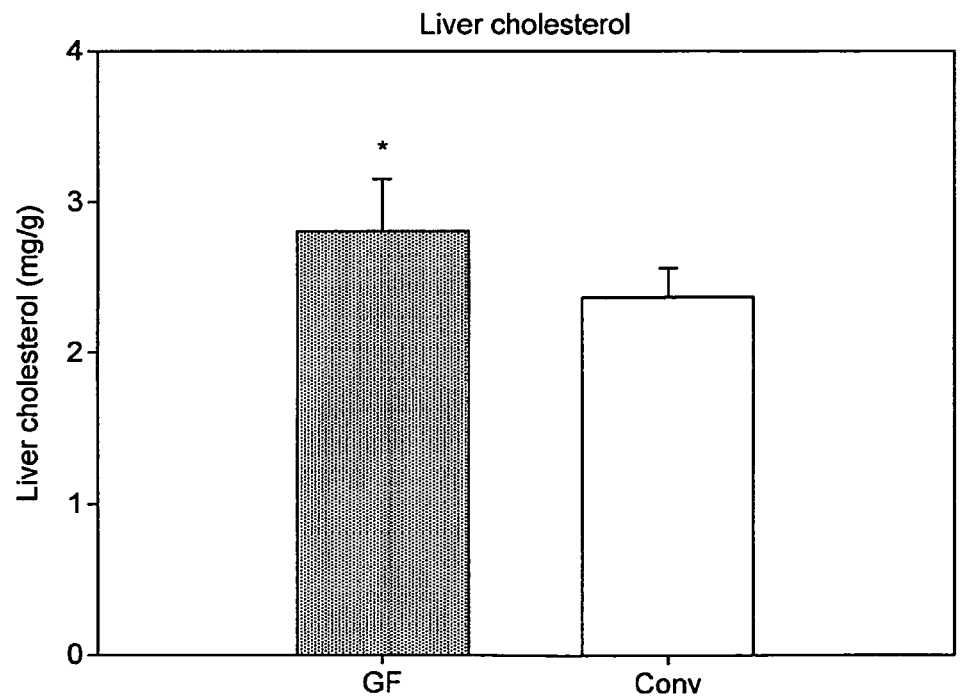
Figure 29:
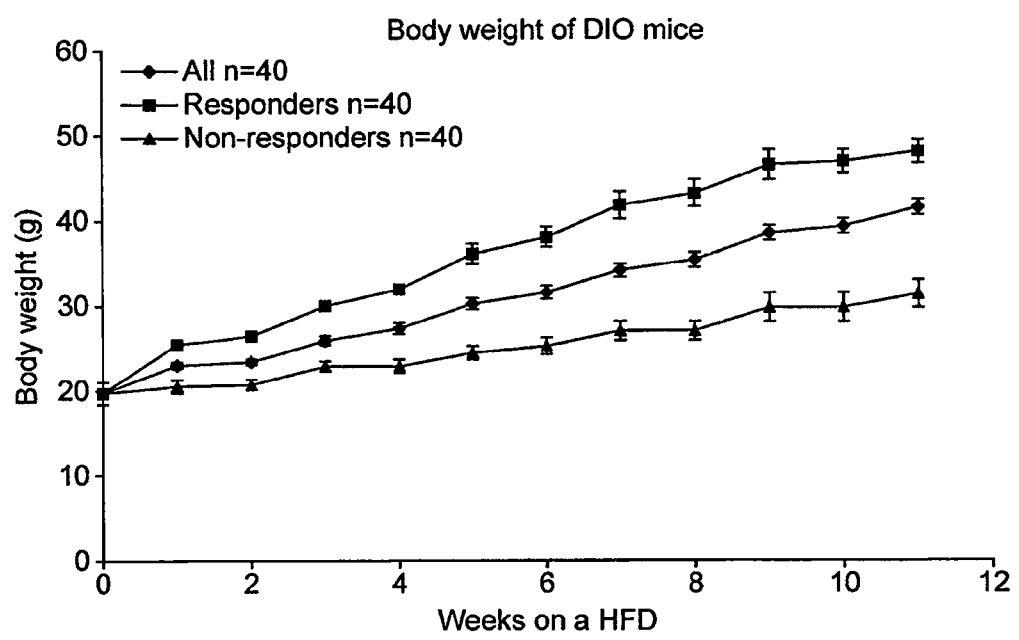

Liver weights were measured during sacrifice. Data are median±semedian, n=14 for germ free mice; n=16 for conventional mice. Kruskal-Wallis test followed by Wilcoxon tests for pair-wise comparisons were applied. * p<0.05 vs conventional mice FIG. 26 shows the liver triglycerides in the germ free and conventional mice one a high fat diet Liver samples were collected during the sacrifice. Total lipids were extracted from the liver samples for triglyceride determination. Data are median±semedian, n=8. Kruskal-Wallis test followed by Wilcoxon tests for pair-wise comparisons were applied. * p<0.05 vs conventional mice FIG. 27 shows the liver glycogen contents in the germ free and conventional mice one a high fat diet Liver samples were collected during the sacrifice. Glycogens were extracted from the liver samples for quantification. Data are median±semedian, n=8. Kruskal-Wallis test followed by Wilcoxon tests for pair-wise comparisons were applied. * p<0.05 vs conventional mice FIG. 28 shows the liver cholesterol contents in the germ free and conventional mice one a high fat diet Liver samples were collected during the sacrifice. Cholesterols were extracted from the liver samples for quantification. Data are median±semedian, n=8. Kruskal-Wallis test followed by Wilcoxon tests for pair-wise comparisons were applied. * p<0.05 vs conventional mice FIG. 29 shows the body weight changes of responders and non-responders on a high fat diet. 40 C57BL/6J mice were fed with a high fat diet for 11 weeks. The four top body weight gainers were defined as responders and the four bottom body weight gainers were defined as non-responders. Data are mean±sem.

Figure 30:
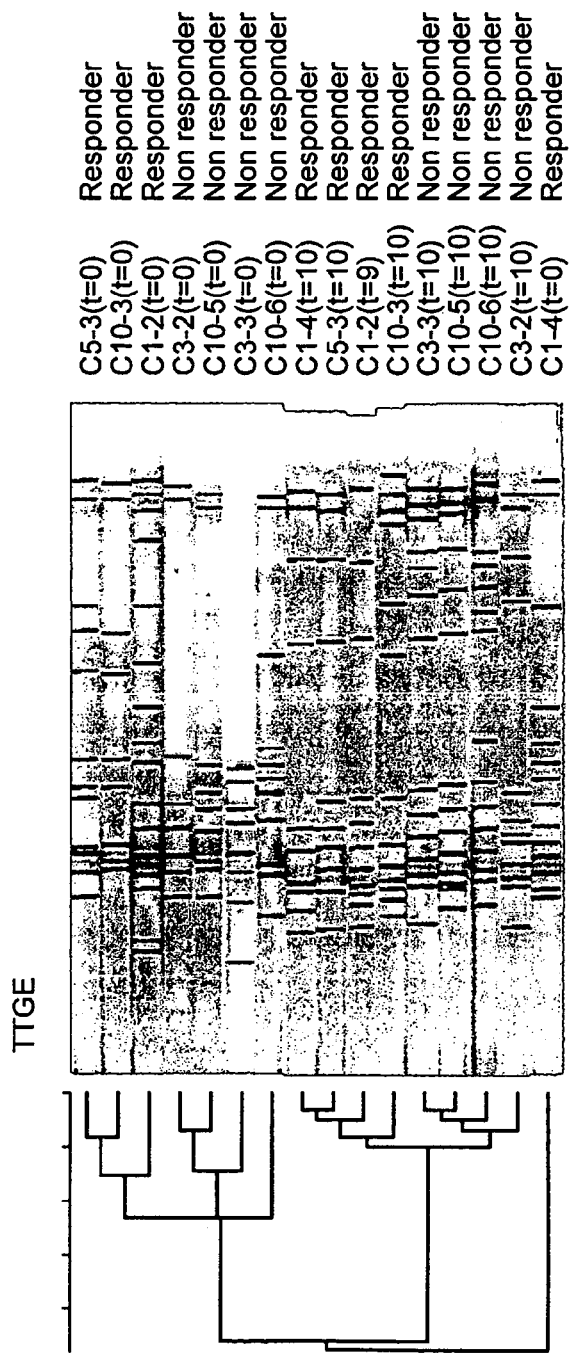

FIG. 30 shows the analysis of fecal microbiota profile in responders and non-responders using temporal temperature gradient gel electrophoresis (TTGE)

Fecal samples were collected before (T0) and after 10-week high fat diet feeding (T10). Fecal bacterial DNAs were isolated and then were amplified by PCR. PCR products were separated based on temperature gradient.

Figure 31:
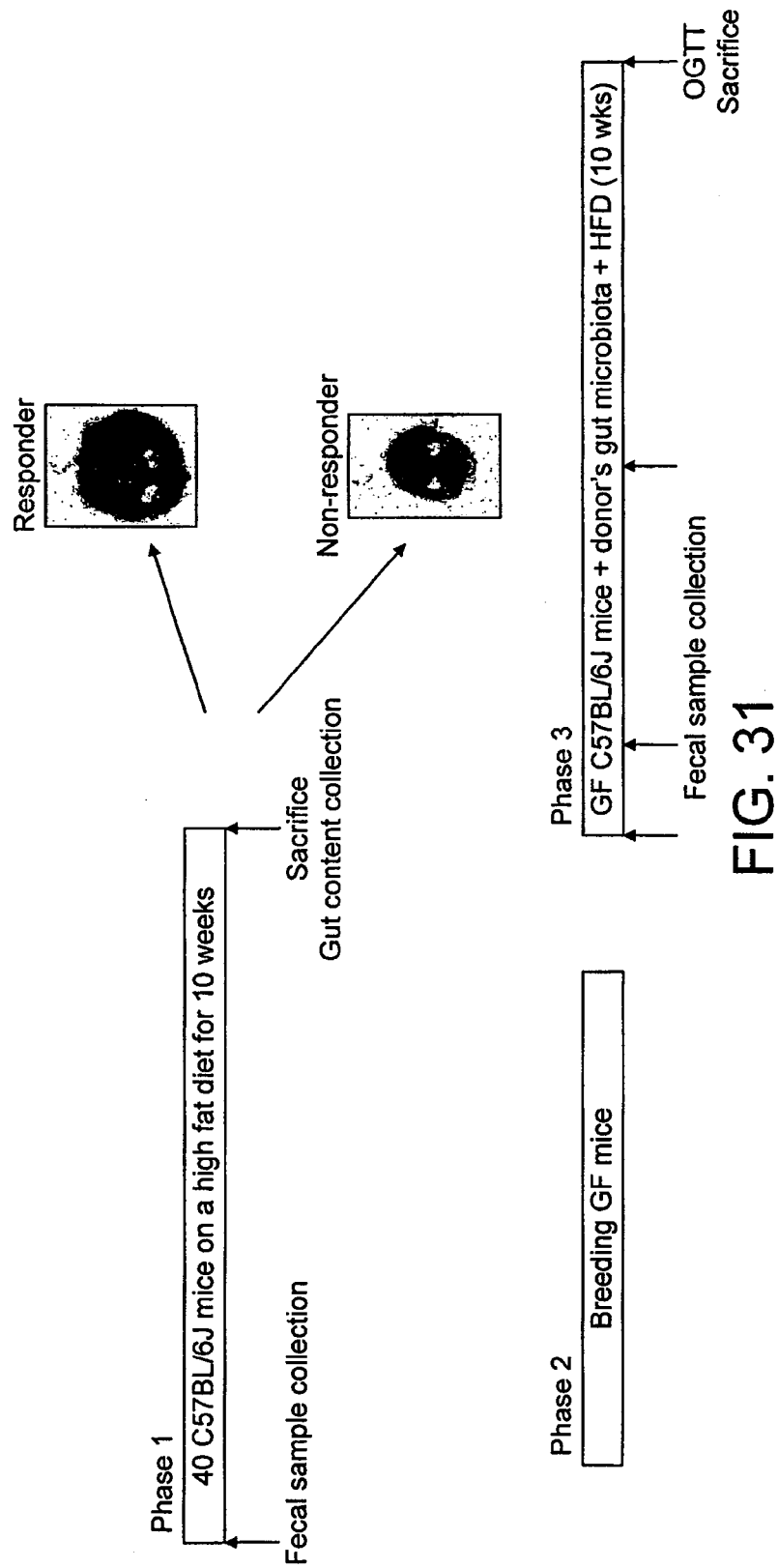
Figure 32:
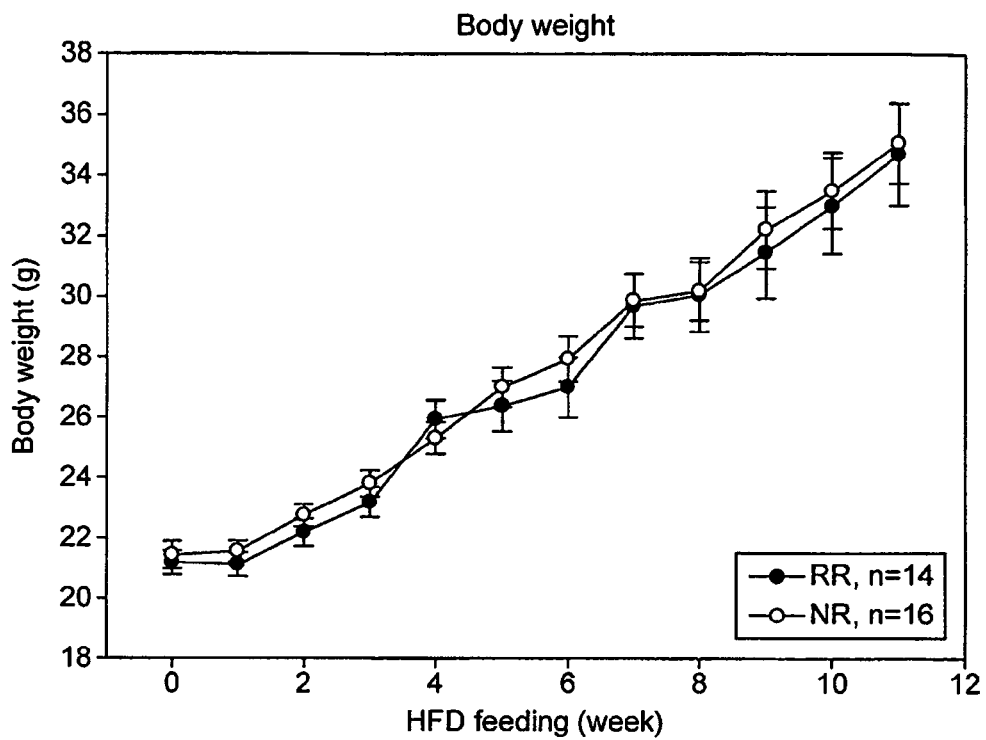

FIG. 31 shows the study design for demonstrating the causal effect of gut microbiota on the development of body weight and insulin resistance FIG. 32 shows the body weight changes of RR and NR mice Body weights were measure once a week for 11 weeks. Data are mean±sem, n=14 for RR mice and n=16 for NR mice.

Figure 33:
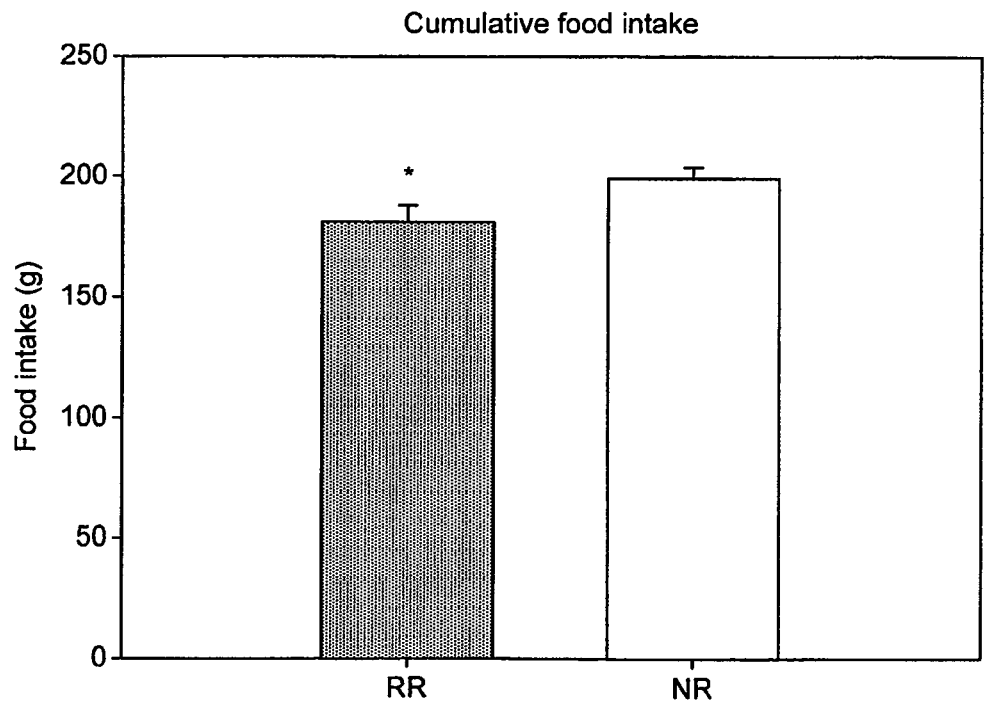

FIG. 33 shows the cumulated food intake of RR and NR mice

Figure 34:
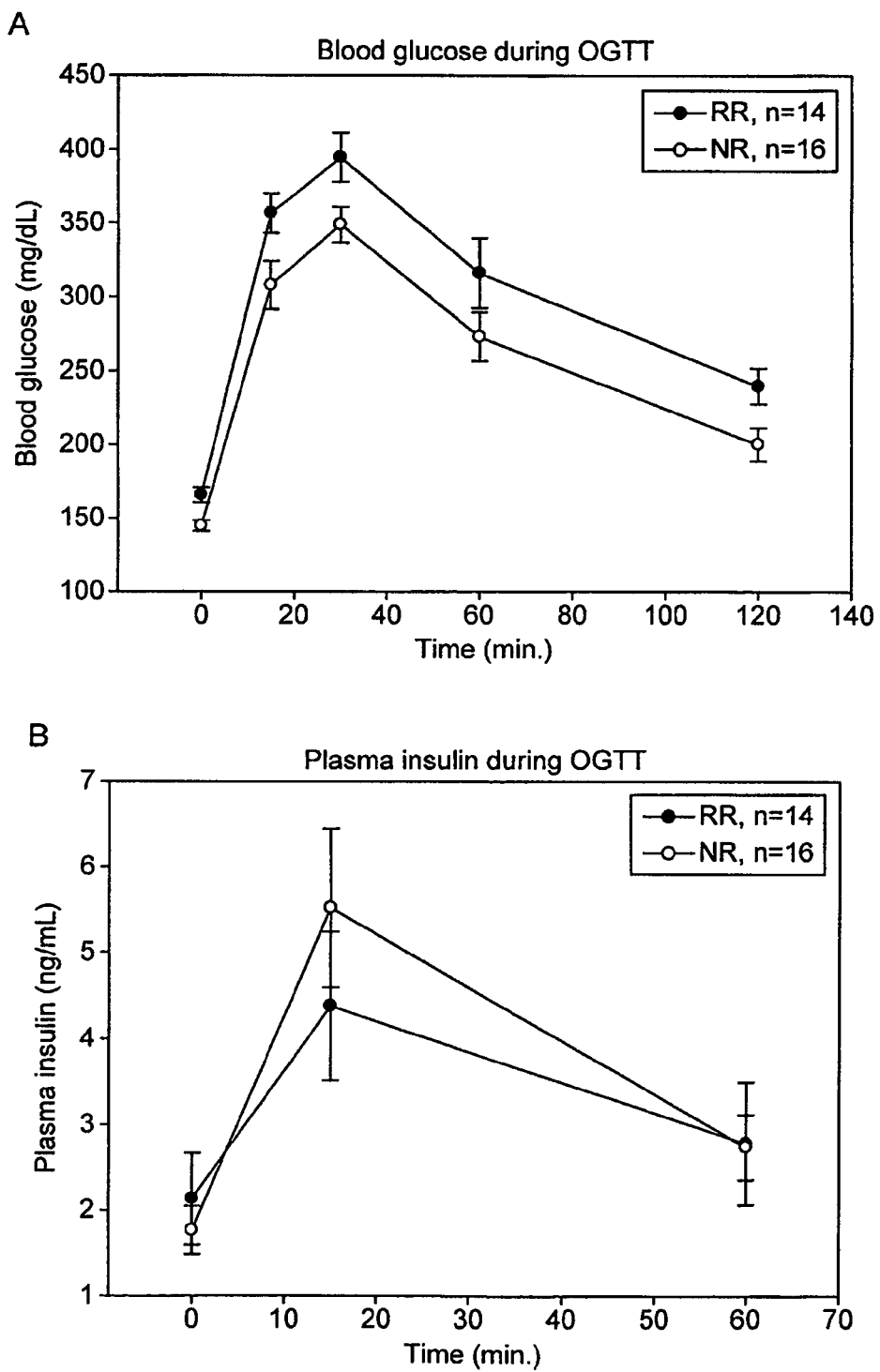

Cumulated food intake were calculated from 11 weekly food intake records. Data are median±semedian, n=14 for RR and n=16 for NR mice. Kruskal-Wallis test followed by Wilcoxon tests for pair-wise comparisons were applied. * p<0.05 vs conventional mice FIG. 34 shows the oral glucose tolerance of RR and NR mice.

Results of blood glucose (A) and plasma insulin excursion (B) are shown. Mice were tested at the end of high fat diet feeding. Data are median±semedian, n=14 for RR and n=16 for NR.

EXAMPLES

Example 1

Male C57BL/6J mice at 7 weeks old were put on a high fat diet for 10 weeks. Then, the mice were randomized into 2 groups (n=5), a control and an antibiotics treated group. Polymyxin B and neomycin were dissolved in drinking water. The doses of polymyxin B and neomycin are 0.5 and 1.0 g/L, respectively. The mice were treated with the antibiotic combination for 2 weeks. At the end of treatment period, mice were fasted for 6 hours from 8:00 before sacrifice started. During the sacrifice, blood glucose levels were determined and cecal contents were collected for assessing the composition of gut bacteria. The cecal content of control and antibiotic treated mice were plated on Drigalski media to determine the number of enterobacteria.

Example 2

Seven to eight weeks-old male obese ob/ob mice were fed a chow diet and treated with $10^9$-$10^{10}$ cfu *Lactobacillus rhamnosus* CGMCC 1.3724 per day for 60 days. *Lactobacillus rhamnosus* CGMCC 1.3724 biomass diluted in the MRS medium was added to the drinking solution containing 0.9% NaCl. The control group received the saline solution with corresponding amount of MRS medium present in the probiotic preparation. Body weight of the mice was followed during the study. The feces of treated and control ob/ob mice were plated on Drigalski media to determine the number of enterobacteria.

Example 3

Beneficial Effect of Gut Microbiota Modulation by Polymyxin B and Neomycin

In example 1, reduction of cecal enterobacteria was observed in a high fat diet induced obese and insulin resistant C57BL/6J (DIO) mice treated with polymyxin B and neomycin. Subsequently, blood glucose concentrations of the treated mice were also reduced, supporting a beneficit of eliminating intestinal enterobacteria. To further examine impacts of gut microbiota modulation by polymyxin B and neomycin in DIO mice, an additional study was conducted. The design of the study consists two parts: the effect of antibiotic treatment (ABT) and the effect of washout (WO). In the ABT period, mice were exposed to a placebo or a combination of polymyxin B (0.5 g/L) and neomycin (1 g/L). Half of mice were sacrificed immediately after the antibiotic treatment and the other half of mice underwent additional 4 wks washout period before sacrifice. FIG. 5 illustrates the design of the study.

Figure 1:
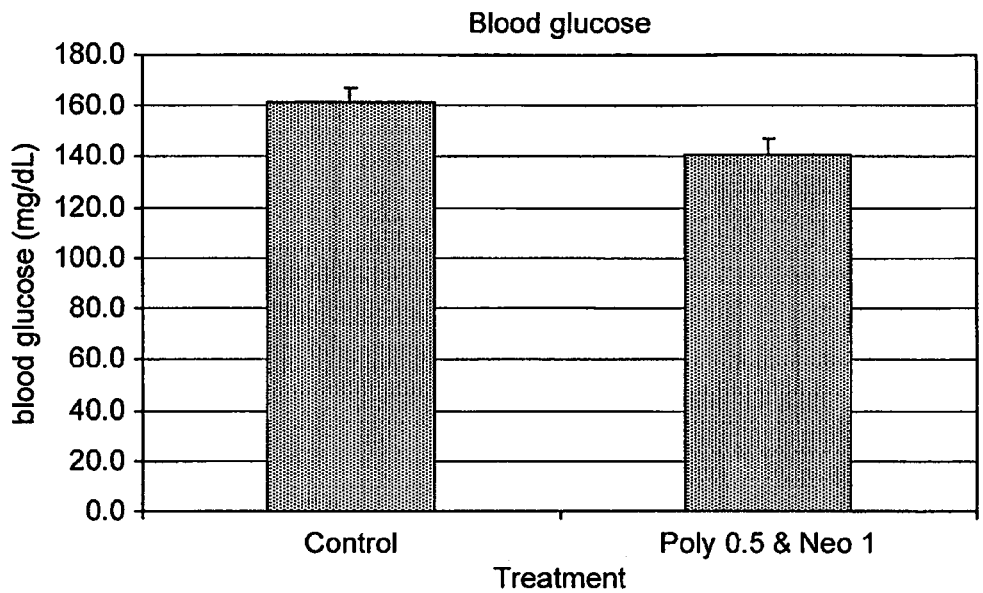
FIG. 1 shows the blood glucose levels of a control group and of mice treated with the antibiotics polymyxin B and neomycin after carrying out the experiment of example 1.
Figure 2:
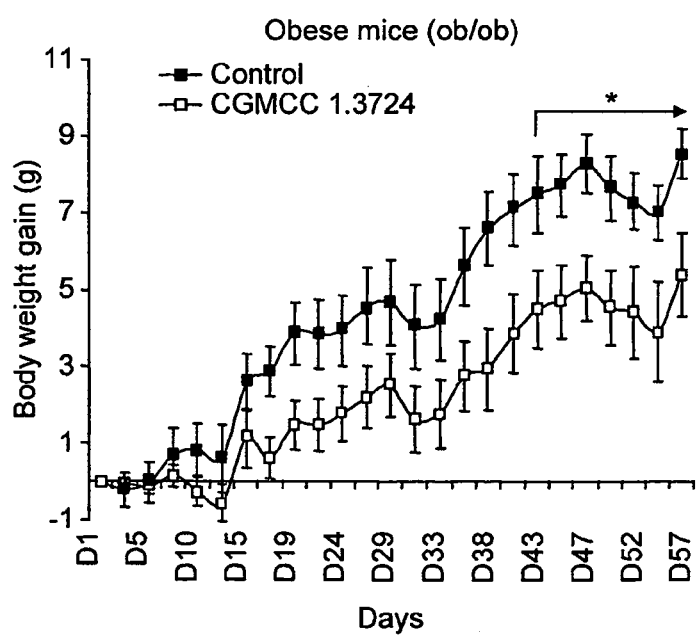
FIG. 2 shows the body weight gain of mice after treatment with Lactobacillus rhamnosus CGMCC 1.3724 in accordance with example 2 and of a control experiment.
Figure 3:
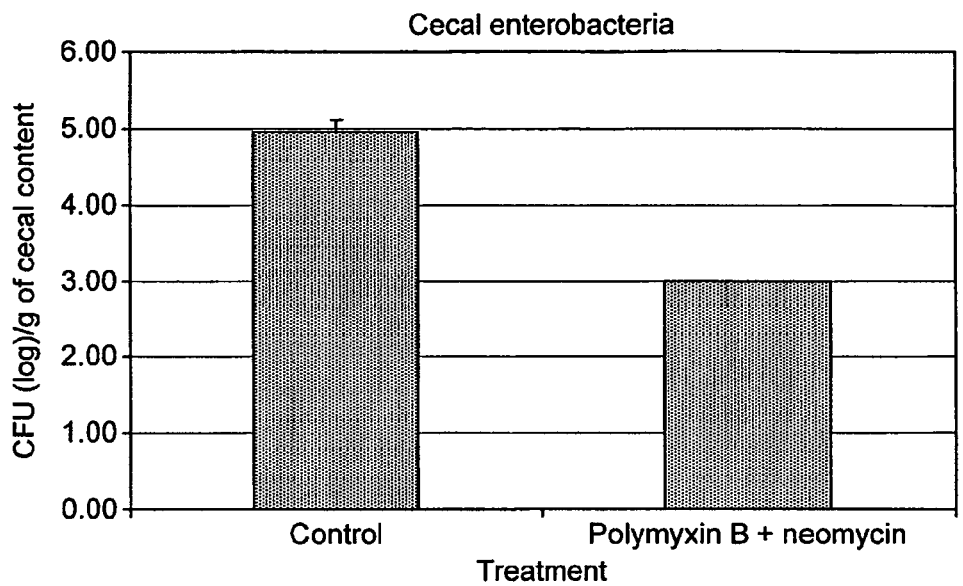
FIG. 3 shows the number of enterobacteria determined in the feces of a control group and of mice treated with the antibiotics polymyxin B and neomycin after carrying out the experiment of example 1.
Figure 4:
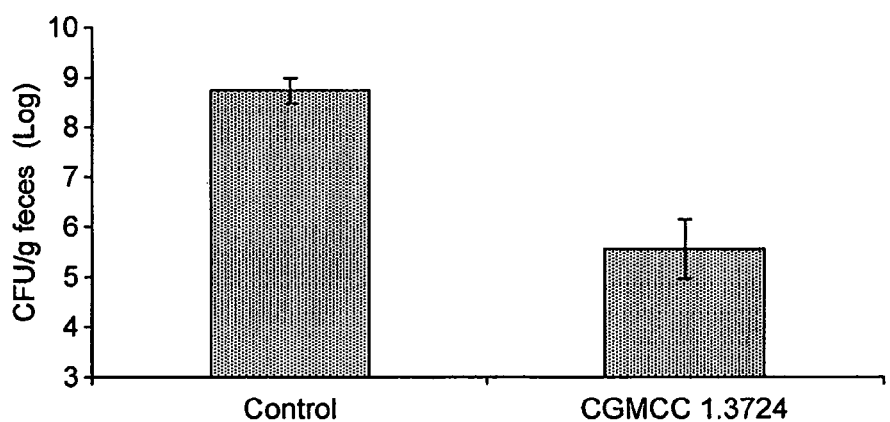
FIG. 4 shows the number of enterobacteria determined in the feces of a control group and of mice with Lactobacillus rhamnosus CGMCC 1.3724 after carrying out the experiment of example 2.

FIG. 6 illustrates the progression of blood glucose concentrations in DIO mice treated with polymyxin B and neomycin. DIO mice treated with placebo remained hyperglycemic throughout the study. In contrast, DIO mice drank the water containing polymyxin B and neomycin showed steady reduction of blood glucose levels. A statistical difference was observed when compared to the control was observed at the end of washout period (FIG. 2A). The DIO mice responded to polymyxin B and neomycin treatment with significant reduction of blood glucose. Most importantly, blood glucose levels went down continuously even when antibiotics were removed from the drinking water (FIG. 2B). These data indicate that a further reduction of blood glucose during the washout period was due to factors independent of antibiotics.

Similar to observed benefit in blood glucose lowering, oral glucose tolerance of the treated DIO mice followed a same pattern. Illustrated in FIG. 7A, a mild reduction in blood glucose excursion during an oral glucose tolerance test (OGTT) was found in the treated DIO mice. The improvement became statistically significant in the treated DIO mice at the of a 4-week washout period (FIG. 7B). The improvement of glucose clearance was independent of plasma insulin because no difference was observed during the OGTT. This data suggest that a persisting factor during the washout period is responsible for the blood glucose lowering effect.

In order to examine whether intestinal bacteria could be responsible for the improved glucose homeostasis, the composition of cecal microbiota was analyzed. FIG. 8 shows the result of cecal microbiota analysis by denatured gradient gel electrophoresis (DGGE). Bacterial gene 16S rDNAs were amplified by polymerase chain reaction (PCR). PCR products were separated in a gradient gel depending on the nucleotide sequence of the 16S rDNA in each bacterial cell. Each band roughly represents one kind of bacteria. The pattern of bands collectively indicates a profile of a complex bacteria population. FIG. 8 shows that gut microbiota was significantly altered by the treatment with polymyxin B and neomycin. More importantly, the pattern of bands or a profile of cecal microbiota, was similar between samples collected after the antibiotic treatment and after the washout. A near identical gut microbiota profile in the treated mice fits the search criteria for a persisting factor that has to be similar from the end of antibiotic treatment period to the end of washout period. In addition, the treatment with polymyxin B and neomycin did not affect the total number of bacteria in the cecum, which was measured by a quantitative PCR technique that amplifies non-discriminately all bacterial specific 16S rDNAs. This result indicates that the polymyxin B and neomycin treatment changed the gut microbiota composition but not the total number of bacteria in DIO mice. The persisting change of gut microbiota during the washout period correlates with a continuous improvement of glycemia in the treated mice.

To further reveal the composition of the polymyxin B and neomycin treated gut microbiota, we built 8 16S rDNA clone libraries using 2 samples from each group. FIG. 9 shows percentage of annotated sequences with Silva databases. Setting an identity threshold as stringent as 99% resulted in a highly reduced number of sequences that were annotated. An identity threshold set at 98% is commonly accepted for discriminating sequences at the species level. To discriminate sequences at the genus level, the identity threshold should be set at 95%. Then a 95% identity threshold and 80% coverage were set for obtaining a balance between accurate taxonomic assignments and a high number of annotated sequences. Then, a 16S classification software, RDP-II Classifier was selected to generate phylogenetic assignments for the sequences. FIG. 10 shows that nearly all sequences were identified at the phylum level. Our data confirm that the composition of gut microbiota changed dramatically after the treatment with polymyxin B and neomycin. Reduction of Proteobacteria and Deferribacteres together with proliferation of Bacteriodetes was observed after the antibiotic treatment. This modified gut microbiota composition was associated with improvement of blood glucose levels in mice with diabetes. In this composition of gut microbiota, the ratios of proteobacteria to bacteriodetes and the ratio of proteobacteria to firmicutes were modified. Modified ratios persisted to the end of washout period. Since all other physiological parameters such as body weight, body fat mass, and food intake were all similar between untreated and treated DIO mice, the changes in certain divisions of bacteria or in ratios between divisions of bacteria would be responsible for the improvement of insulin sensitivity in the animals.

Example 3

In Vitro Antibiotic Susceptibility Tests

Antimicrobial susceptibility of selected intestinal bacterial groups (*lactobacilli*, bifidobacteria, bacteroides, and Enterobacteria) was determined by the strip test according to the manufacture's instructions (AB Biodisk, Solna, Sweden). Briefly, feces of ob/ob mice were diluted in Ringer/cystein solution and plated on specific media. One colony of each selected bacterial group was used to prepare the bacterial inocula for the susceptibility tests. The bacterial suspensions were swabbed onto specific media: *Brucella* agar for bacteroides, Mueller Hinton agar for Enterobacteria, and MRS/cystein agar for *lactobacilli* and bifidobacteria. Antibiotic strips containing serial dilutions of antibiotics were applied to the agar surface, and plates were incubated at 37° C. for 24 or 48 hours in aerobic and anaerobic conditions, respectively. The preformed concentration gradient of antibiotic (amoxicillin, ampicillin or norfloxacin) is immediately transferred to the agar medium, and forms a symmetrical inhibition ellipse centered along the strip. The minimum inhibitory concentration is read directly from the scale at the point where the edge of inhibition ellipse intersects the strip. Bacterial groups were considered sensitive (S) or resistant (R) to the antibiotic according to a scale provided by the manufacturer.

Table 1 shows that Norfloxacin was capable of suppressing the growth of fecal enterobacteria. Enterobacteria were resistant to amoxicillin and were only partially sensitive to ampicillin. Results indicate that specific antibiotics are needed when enterobacteria are a target for deletion. A combination of norfloxacin and ampicillin suppressed the growth of enterobacteria, bacteroides, lactobacillus and bifidobacteria.

TABLE 1

Result of in vitro antibiotic susceptibility tests

| | Amoxicillin | Ampicillin | Norfloxacin |
|---|---|---|---|
| Enterobacteria | R (0/19) | S/R (13/19) | S (19/19) |
| Bacteroides | S/R (14/16) | S (16/16) | R (0/16) |
| Lactobacillus | S (33/33) | S (33/33) | S/R (25/33) |
| Bifidobacteria | S (3/3) | S (3/3) | R (0/3) |

Example 4

In Vivo Dose Determination Study in ob/ob Mice 8 to 10 wk old male ob/ob mice (Charles River Laboratories, Inc. France) were treated with a combination of norfloxacin and ampicillin at 0, 0.2, 1 or 2 g/L for each antibiotic in their drinking water for 14 days (n=6/group). All the mice were housed individually and provided with a sterile chow diet (diet 3434, Kliba Nafag, Basel, Switzerland) and sterile water ad libitum. At the end of the treatment, mice were sacrificed at 9:00 hrs without food deprivation. Blood samples were collected for biochemical analyses. Liver and jejunum were collected for gene expression analyses. Liver total triglycerides and glycogen contents were also determined, while cecal content was exclusively used for the assessment of total bacteria.

Total aerobic and anaerobic bacteria were enumerated in selective media and incubation conditions. In brief, cecal samples were diluted in Ringer medium and total aerobic and anaerobic bacteria were investigated by plating onto nonselective media: TSS medium (Biomerieux, Lyon, France) for 24 to 48 hrs at 37° C. in aerobic and anaerobic conditions. Bacterial numbers were expressed as colony forming units (CFU)/mg cecal content.

FIG. 11 depicts an illustration on the dose dependent effect of norfloxacin and ampicillin on the suppression of cecal aerobic bacteria (FIG. 11A) and cecal anaerobic bacteria (FIG. 11B). Clear reduction of cecal aerobic and anaerobic bacteria indicates that the population of gut microbiota was diminished by oral feeding of norfloxacin and ampicillin to ob/ob mice. Since enterobacteria are facultative anaerobic bacteria and grow well in aerobic environment or anaerobic environment, that reduction of bacterial counts in both conditions suggests a decrease in cecal enterobacteria population.

Table 2 show the benefits of gut microbiota reduction in the improvement of blood glucose, liver glycogen and liver triglycerides in animals with obesity and insulin resistance.

ally. After 2 wks of habituation, mice were randomized based on their body weight and blood glucose concentrations into 3 groups (n=12/group): 1) the control group with free access to sterile food; 2) antibiotic treated group given norfloxacin and ampicillin in drinking water (1 g/l each) with free access to sterile food and water; and 3) a pair-fed group consuming the same amount of food as the antibiotic treated group does (FIG. 12). Throughout the 17 day treatment period, body weight, water and food intake were recorded daily. Pair-feeding was accomplished by measuring the 24-hr food intake of each antibiotic treated mouse throughout the experimental period. In the following day, the pair-fed mice received the same amount of food as that which their matched mouse in the antibiotic treated group consumed. The food was divided in 2 equal portions that were provided at 8:00 and 17:00 hrs. Oral glucose tolerance tests (OGTT) were conducted in overnight fasted (15 hr) mice on day 13. On day 17, overnight fasted mice were sacrificed for tissue sample collection. Blood glucose concentrations were measured before anesthesia by tail incision using an Ascensia Elite XL glucometer (Bayer AG, Zurich, Switzerland). Epididymal and retroperitoneal adipose tissues, liver, pancreas, gastrointestinal (GI) tract from stomach to anus, and cecal content were collected in animals immediately after being exsanguinated via a cardiac puncture and flash frozen in liquid nitrogen.

FIG. 13A shows the reduction of cecal enterobacteria in the ob/ob mice treated with norfloxacin and ampicillin. The data confirm the observation in Example 4 that a successful reduction of intestinal enterobacteria was achieved by giving norfloxacin and ampicillin. More importantly, plasma lipopolysaccharide (LPS) concentrations were also reduced

TABLE 2

Dose dependent effects of the antibiotic treatment in ob/ob mice

| | Body weight (g) | Cumulative food intake (g) | Blood glucose (mg/dL) | Liver glycogen (mg/g liver) | Liver triglycerides (µg/g liver) |
|---|---|---|---|---|---|
| 0 g/L | 47.9 ± 1.6 | 98.0 ± 9.6 | 158.5 ± 43.8 | 37.5 ± 6.1 | 162.8 ± 7.9 |
| 0.2 g/L | 46.3 ± 1.0 | 80.6 ± 6.3 | 133.0 ± 17.1 | 49.9 ± 2.7* | 134.3 ± 6.1* |
| 1.0 g/L | 47.2 ± 2.0 | 78.5 ± 8.3 | 92.5 ± 4.6* | 58.9 ± 4.6* | 117.1 ± 0.8* |
| 2.0 g/L | 45.9 ± 2.5 | 75.7 ± 3.8* | 109.0 ± 15.5 | 47.7 ± 2.8 | 131.2 ± 13* |

Norfloxacin and ampicillin were added to the drinking water at the concentrations indicated in the table.
Data are median ± semdeian, n = 6.
*p < 0.05 vs. 0 g/L Elevated blood glucose and reduced liver glycogen are common symptom of type 2 diabetes. Suppression of gut microbiota by norfloxacin and ampicillin significantly reversed the two metabolic abnormalities of diabetes. Liver triglycerides were also reduced by the antibiotic treatments (Table 2). High amount of liver triglycerides, a condition called hepatic steatosis, is commonly found in patients with obesity or type 2 diabetes, and hepatic steatosis is known to induce liver insulin resistance. Our results show that excessive accumulation of fat in the liver can be reduced by the gut microbiota reduction.

Example 5

Efficacy of Gut Microbiota Reduction by Norfloxacin and Ampicillin on Oral Glucose Tolerance of ob/ob Mice Thirty-six 8-10 wk old male ob/ob mice (Charles River Laboratories Inc., France) were fed a sterile chow diet (diet 3434, Kliba Nafag, Basel, Switzerland) and housed individu- (FIG. 13B). LPS presents only on the cell wall surface of Gram negative bacteria. Reduction of plasma LPS correlates with a reduced number of enterobacteria in the intestine. Our results indicate that removal of intestinal enterobacteria led to a significant decrease in plasma LPS concentration.

FIG. 14 illustrates the improvement of antibiotic treatment by norfloxacin and ampicillin in the oral glucose tolerance of ob/ob mice. A 2-week treatment normalized the hyperglycaemia of ob/ob as the baseline blood glucose level before OGTTs dropped below 100 mg/dL. After challenged with an oral glucose load, the treated ob/ob mice also showed a much rapid clearance of blood glucose as compared to either untreated control or pair-fed control (FIG. 14A). Quantification of the blood glucose values under the curve are shown in FIG. 14B. Plasma insulin concentrations during the OGTT were also reduced in the treated mice (FIG. 15A). Total insulin secreted during the OGTT was significantly lower in the ob/ob treated with antibiotics (FIG. 15B). Marked reduction of blood glucose and plasma insulin levels during OGTTs indicate a much improved insulin sensitivity in the ob/ob mice receiving the treatment of gut microbiota reduction with norfloxacin and ampicillin.

FIG. 16 shows the improvement of glycemic control in the treated ob/ob mice. Due to insulin resistance, diabetic subjects have elevated blood glucose levels in the fasting and non-fasting state. In untreated animals, blood glucose was at abnormal levels reflecting the diabetic state of ob/ob mice. In contrast, the ob/ob mice received the antibiotic treatment had much reduced blood glucose levels at the fasting and non-fasting condition (FIG. 16A).

Liver glycogen is usually elevated after eating and reduced after prolonged fasting. However, in a diabetic condition, liver glycogen storage is low even after a meal is taken. A lack of liver glycogen synthesis is one of many reasons for elevated blood glucose concentrations in diabetic patients. In FIG. 16B, our results clearly showed that diabetic mice treated with gut microbiota reduction with norfloxacin and ampicillin significantly recovered the capability of making and storing liver glycogen.

FIG. 17 showed an amelioration of hepatic steatosis in the ob/ob mice receiving gut microbiota reduction. Accumulation of liver triglycerides is a commonly found in patients with insulin resistance and type 2 diabetes, which is a condition called non-alcohol hepatic steatosis (NAFLD). NAFLD can progress to a much severe pathological state NASH and eventually to liver cirrhosis. Up to date, very few treatments are available for NAFLD. In the present example, untreated ob/ob mice showed an excessive amount of liver fat accumulation. The treatment with norfloxacin and ampicillin significantly reduced NAFLD in ob/ob mice. This result indicate that removal of gut microbiota and intestinal enterobacteria markedly alleviated many metabolic abnormalities such as insulin resistance, hyperglycemia, low liver glycogen and NAFLD that are commonly associated with type 2 diabetes and obesity.

Example 6

Mice Without Gut Microbiota are Resistant to High Fat Diet-Induced Obesity and Insulin Resistance Data in Example 5 show that reduction of gut microbiota normalized the insulin resistance in ob/ob mice. In the present example, we demonstrate that lack of bacteria in the gut prevents the development of obesity and insulin resistance. Germ free and conventional C57BL/6J mice (n=16/group) were fed with a sterile high fat diet for 11 weeks. Germ free mice were kept in a germ free isolator throughout the study, and conventional mice were kept in the same room. At the end of study, germ free mice were taken out of the isolator for oral glucose tolerance tests (OGTT). Before OGTT, both germ free and conventional control mice were deprived for food for 6 hours. Three hours after the end of OGTT, all mice were sacrificed and tissues were collected for analysis. Feces of germ free mice were collected once a week for fecal bacteria analysis. No live bacteria were found in all fecal samples of the germ free mice, which confirmed a germ free status of the mice.

FIG. 18 illustrates the body weight gain of germ free and conventional mice when eating a sterile high fat diet. Data clearly shows that germ free mice living inside of an isolator gained much less weight than the conventional mice did. At the end of 11-week feeding, conventional mice were 9 gram heavier than germ free mice.

FIG. 19 illustrates the cumulative food intake of germ free and conventional mice when eat a high fat diet. Germ free mice ate less than conventional mice did.

FIG. 20 illustrates the total fat pad weight in germ free or conventional mice. The total fat pad includes epididymal fat pad, mesenteric fat pad and retroperitoneal fat pad. The sum of 3 fat pads represent a majority of visceral fat. Germ free mice have much less fat pad weight than the conventional mice. Results indicate that germ free mice weight less and leaner than the conventional mice when eating a high fat diet.

FIGS. 21, 22 and 23 illustrate the plasma free fatty acids, plasma total cholesterol and plasma triglycerides, respectively. In all three parameters, the values in the germ free mice were significantly lower. Results indicate that not only the germ free mice were leaner, they were metabolic healthier than the convention mice.

FIG. 24 illustrates the response of the germ free and conventional DIO mice to an oral glucose challenge. In contrast to conventional DIO mice, germ free mice were glucose tolerant. The blood glucose excursion was significantly reduced in the germ free mice (FIG. 24A). Corresponding plasma insulin values during the OGTT were also much reduced in the germ free mice (FIG. 24B). These results indicate that germ free mice were also resistant to high fat diet-induced insulin resistance.

FIG. 25 illustrates the liver weight in the germ free and conventional DIO mice. Results clearly indicate that the liver weighed less in the germ free than in the conventional mice. Also, liver triglycerides (FIG. 26) and liver glycogen contents (FIG. 27) were also decreased in the germ free mice suggesting that the energy store in the germ free liver was also reduced. In contrast to the energy store, liver cholesterol levels were higher in the germ free than in the conventional DIO mice (FIG. 28). A high level of liver cholesterol might be due to an increase of de novo cholesterol biosynthesis. The regulation of cholesterol biosynthesis in the liver depends on the plasma cholesterol concentration. In the germ free mice, a low circulating cholesterol level might function as a signal to stimulate the production of cholesterol in the liver. A gene expression analysis in the liver is required to confirm the activation of de novo cholesterol synthesis in the liver.

Table 3 lists the most differentially regulated genes in the liver of germ free mice when compared to the conventional DIO mice.

TABLE 3

A list of liver genes differentially expressed in the germ free mice

| | | |
|---|---|---|
| 2.5 | SLC39A4 (includes EG:55630) | solute carrier family 39 (zinc transporter), member 4 |
| 2.4 | SQLE | squalene epoxidase |
| 2.3 | IGFBP1 | insulin-like growth factor binding protein 1 |
| 2.3 | TFF3 | trefoil factor 3 (intestinal) |
| 2.2 | IGFBP2 | insulin-like growth factor binding protein 2, 36 kDa |
| 2.2 | SC4MOL | sterol-C4-methyl oxidase-like |
| 2.1 | EGR1 | early growth response 1 |
| 2.0 | HMGCS1 | 3-hydroxy-3-methylglutaryl-Coenzyme A synthase 1 (soluble) |
| 2.0 | ELA2A | elastase 2A |
| 2.0 | TP53INP1 | tumor protein p53 inducible nuclear protein 1 |
| −2.1 | LGALS1 | lectin, galactoside-binding, soluble, 1 (galectin 1) |
| −2.1 | LCN2 | lipocalin 2 |
| −2.2 | SAA2 | serum amyloid A2 |
| −2.2 | ME1 | malic enzyme 1, NADP(+)-dependent, cytosolic |
| −2.2 | AATK | apoptosis-associated tyrosine kinase |
| −2.3 | HAMP | hepcidin antimicrobial peptide |

TABLE 3-continued

A list of liver genes differentially expressed in the germ free mice

| -2.6 | WFDC2 | WAP four-disulfide core domain 2 |
|---|---|---|
| -2.6 | CSAD | cysteine sulfinic acid decarboxylase |
| -3.0 | CFD | complement factor D (adipsin) |
| -3.1 | CYP2B6/CYP2B10 | cytochrome P450, family 2, subfamily B, polypeptide 6 |

Liver samples were collected during the sacrifice. Total liver RNA were extracted and gene expression analysis was done with using Mouse Ref-8 V1.1 expression beadchips. Bioinformatics were done with Ingenuity software.

Liver total RNA were extracted and nineteen thousand genes were examined by using Illumina Mouse Ref-8 V1.1 expression beadchips. Data were expressed as folds of change when comparing the expression of genes in germ free to conventional mice. Positive numbers indicate that the gene is highly expressed in the germ free liver, and negative numbers represent that the gene had reduced expression in the germ free liver. Many genes involved in cholesterol metabolism (SQLE. SC4MOL and HMGCS1) and growth and development (IGFBP 1 and IGFBP2) were up-regulated in the germ free liver. The up-regulation of genes in cholesterol biosynthesis pathway supports the observations of low plasma cholesterol and high liver cholesterol levels in the germ free mice. Genes (LGALS1, LCN2, SAA2, HAMP and CFD) involved in inflammation and bacterial stimulated responses were down-regulated in the germ free liver.

In this example, our results show that lack of bacteria in the intestine led to a lean and insulin sensitive phenotype even when the mice were challenged by a high fat diet. Also, germ free animals are metabolically healthier than the conventional mice. Our results support the idea that reducing certain bacteria in the gut is beneficial for obesity and type 2 diabetes.

Example 7

Gut Microbiota Directly Affects the Development of Insulin Resistance in DIO Mice In example 6, our data show that germ free mice were resistant to high fat diet-induced obesity and insulin resistance. In this example, we designed a study to demonstrate that gut microbiota directly contribute to the development of obesity and insulin resistance. We inoculated 2 different compositions of gut microbiota to germ free mice and examined the weight gain performance and oral glucose tolerance of the ex-germ free mice.

The selection of gut microbiota donors were based on the body weight and blood glucose concentration of the DIO mice. FIG. 29 illustrates a diverse response of C57BL/6J mice to high fat diet feeding. A subgroup of DIO mice gained significantly more weight than the average of the cohort (Responders). The other subgroup of DIO mice gained significantly less weight than the whole cohort (Non-responders). The difference in the body weight between the responders and non-responders were near 20 grams. Since all mice have identical genetic background, we hypothesized that a different gut microbiota composition is the cause of the differential weight gains to the high fat diet challenge. Before testing this hypothesis, it is necessary to demonstrate that responders and non-responders have different intestinal microbiota composition.

FIG. 30 shows that responders and non-responders had different fecal microbiota compositions. Fecal bacterial DNAs were extracted and bacterial specific 16S rDNAs were amplified by PCR. The products of PCR were then separated on a temperature gradient gel, and each band represents one kind of bacteria. A pattern of bands indicates a composition of different bacteria. Results show that two major clusters were separated by the effect of high fat diet feeding (T0 vs T10). Ten weeks of a high fat diet feeding significantly altered the composition of fecal microbiota. Within each cluster, responders and non-responders formed a sub-cluster. These data indicate that responders and non-responders have a different composition of fecal microbiota regardless whether the mice were eating a chow or a high fat diet.

To test whether different gut microbiota populations in the responder and non-responder mice are responsible for the weight gain, responders and non-responders were identified in a cohort of 40 C57BL/6J mice eating a high fat diet in a conventional environment for 11 weeks. The design of the experiment is illustrated in FIG. 31. One responder donor (RD) and one non-responder donor (ND) were selected based on body weight and blood glucose levels. Donors were sacrificed, and their cecal contents were inoculated to germ free mice. The germ free mice receiving RD's cecal bacteria were called responder receivers (RR), and the germ free mice receiving ND's cecal bacteria were called non-responder receivers (NR). RR and NR mice were kept in different isolators and fed with a sterile high fat diet for 11 weeks.

FIG. 32 shows the body weight changes of RR and NR mice. In contrast to their respective donor, RR and NR mice weighed similarly at the end of high fat diet feeding. The rate of weight gain was also identical in the two groups. These data suggest that providing different compositions of gut microbiota did not affect the body weight accumulation in mice.

FIG. 33 illustrates cumulative food intake of RR and NR mice during 11-week high fat diet feeding. Interestingly, RR mice ate less than NR mice. Since both groups of mice weighed the same, RR mice gained a similar amount of weight by eating less food. These results suggest that the responder's gut microbiota improved energy harvesting and nutrient digestion/absorption in the mice. Increased energy absorption would contribute to the development of obesity if food intake is equal.

FIG. 34 illustrates the results of oral glucose tolerance in RR and NR mice. In contrast to the body weight data, NR mice had a smaller blood glucose excursion after the oral glucose challenge (FIG. 34A). Since RD and ND's blood glucose levels were 223.2 and 158.4 mg/dL, respectively, the degree of oral glucose tolerance in RR or NR mice correlates with the donor's blood glucose concentrations. The reduction of blood glucose excursion was independent of insulin secretion because plasma insulin concentrations were similar between RR and NR mice during the OGTT (FIG. 34B). These data strongly indicate that development of insulin resistance is a transmissible trait through gut microbiota.

Table 4 lists the most differentially regulated genes in the liver of RR and NR mice. Liver total RNA were extracted and nineteen thousand genes were examined by using Illumina whole genome expression with Mouse Ref-8 V1.1 expression beadchips. Data were expressed as folds of change when comparing the expression of liver genes in RR to NR mice. Positive numbers indicate a high level of expression in the RR liver, and negative numbers represent a low level of expression in the RR liver.

TABLE 4

A list of liver genes differentially expressed in the RR mice when comparing to NR mice

| 1.5 | APCS | amylold P component, serum |
|---|---|---|
| 1.5 | SAA1 | serum amyloid A1 |

TABLE 4-continued

A list of liver genes differentially expressed in the RR mice when comparing to NR mice

| | | |
|---|---|---|
| 1.3 | ITIH4 | inter-alpha (globulin) inhibitor H4 (plasma Kallikrein-sensitive glycoprotein) |
| 1.2 | ORM1 | orosomucoid 1 |
| 1.1 | TNFRSF1A | tumor necrosis factor receptor superfamily, member 1A |
| 1.1 | RBP1 | retinol binding protein 1, cellular |
| 1.1 | CALU | calumenin |
| 1.1 | SERPINA3 | serpin peptidase inhibitor, clade A (alpha-1 antiproteinase, antitrypsin), member 3 |
| 1.1 | ITIH3 | Inter-alpha (globulin) inhibitor H3 |
| 1.1 | MYD88 | myeloid differentiation primary response gene (88) |
| 1.1 | SOCS3 | suppressor of cytokine signaling 3 |
| 1.1 | IKBKE | inhibitor of kappa light polypeptide gene enhancer in B-cells, kinase epsilon |
| 1.1 | ORM2 | orosomucoid 2 |
| −1.1 | MAPK9 | mitogen-activated protein kinase 9 |
| −1.1 | MAP2K3 | mitogen-activated protein kinase kinase 3 |
| −1.2 | IL18 | Interleukin 18 (interferon-gamma-inducing factor) |

Liver samples were collected during the sacrifice. Total liver RNA were extracted and gene expression analysis was done with using Mouse Ref-8 V1.1 expression beadchips. Bioinformatics were done with Ingenuity software.

The most up-regulated liver genes (APCS, SAA1, ITIH4 and ORM1) are involved in inflammatory responses. These data indicate that the responder's gut microbiota induced a high level of inflammatory responses in the liver of the recipient mice. Obesity and diabetic patients have elevated systemic inflammation markers, and the low grade inflammation has been shown to induce insulin resistance. Our data suggest that different gut microbiota could have profound impacts on the insulin resistance obese and/or type 2 diabetic patients.

The invention claimed is:

1. A method to treat a metabolic disorder, to support weight loss and/or to support weight management comprising the step of administering to a patient in need of same a composition comprising an effective amount of an an agent that reduces the amount of at least one bacteria selected from the group consisting of proteobacteria and deferribacteres in the gut of the patient such that a ratio of proteobacteria to bacteriodetes in the gut is reduced to a range from 0 to 0.03, wherein the agent comprises an isolated culture of *Lactobacillus rhamnosus* CGMCC 1.3724.

2. The method in accordance with claim 1, wherein the agent increases a ratio of proteobacteria to firmicutes in the gut to a range from 0.05 to 2.

3. The method in accordance with claim 1, wherein the agent increases a ratio of bacteriodetes to firmicutes in the gut to a range from 1.5 to 30.

4. The method in accordance with claim 1, wherein the patient suffers from a disorder selected from the group consisting of obesity, insulin resistance, type-2 diabetes, hyperglycemia, hepatic steatosis, and weight gain.

5. The method in accordance with claim 1, wherein the composition is selected from the group consisting of a medicament and a food product.

6. The method in accordance with claim 1, wherein the patient is selected from the group consisting of infants, children, adolescents and adults.

7. The method in accordance with claim 1, wherein the composition comprises at least one range selected from the group consisting of between $10^2$ and $10^{12}$ cells of the *Lactobacillus rhamnosus* CGMCC 1.3724 per g of the dry weight of the composition, and between $10^2$ and $10^{12}$ cfu of the *Lactobacillus rhamnosus* CGMCC 1.3724 per g of the dry weight of the composition.

8. The method in accordance with claim 1, wherein the composition is a food product selected from the group consisting of milk-powder based products; instant drinks; ready-to-drink formulations; nutritional powders; milk-based products, cereal products; beverages; water; coffee; cappuccino; malt drinks; chocolate flavoured drinks; culinary products and soups.

9. The method of claim 1, wherein the bacteria is selected from the group consisting of gamma-proteobacteria and enterobacteria.

10. The method of claim 1, wherein the patient is selected from the group consisting of humans, pets, and livestock.

11. The method in accordance with claim 1, wherein the agent reduces a ratio of gamma-proteobacteria to bacteriodetes in the gut to a range from 0 to 0.03.

12. The method in accordance with claim 1, wherein the agent increases a ratio of gamma-proteobacteria to firmicutes in the gut to a range from 0.5 to 2.

13. The method in accordance with claim 1, wherein the agent reduces an amount of enterobacteria relative to a total amount of bacteria in the gut by 75-100% based on cfu.

14. The method in accordance with claim 1, wherein administration of the composition treats a metabolic disorder and maintains a total body weight of the patient.

15. The method in accordance with claim 1, wherein the *Lactobacillus rhamnosus* CGMCC 1.3724 within the composition is administered to the patient in an amount selected from the group consisting of $10^4$-$10^{12}$ cfu per day and $10^4$-$10^{12}$ cells per day.

16. The method in accordance with claim 1, wherein the *Lactobacillus rhamnosus* CGMCC 1.3724 within the composition is administered to the patient in an amount selected from the group consisting of $10^9$-$10^{10}$ cfu per day and $10^9$-$10^{10}$ cells per day.

17. A method for treating a disorder selected from the group consisting of obesity, insulin resistance, type-2 diabetes, hyperglycemia, hepatic steatosis, and weight gain comprising the step of administering to a patient having same a composition comprising an effective amount of an an agent that reduces the amount of at least one bacteria selected from the group consisting of proteobacteria and deferribacteres in the gut of the patient such that a ratio of proteobacteria to bacteriodetes in the gut is reduced to a range from 0 to 0.03, wherein the agent comprises an isolated culture of *Lactobacillus rhamnosus* CGMCC 1.3724.

* * * * *